US012694953B2

(12) United States Patent
Woodbury et al.

(10) Patent No.: US 12,694,953 B2
(45) Date of Patent: Jul. 28, 2026

(54) SYSTEMS, METHODS, AND MEDIA FOR MOLECULE DESIGN USING MACHINE LEARNING MECHANISMS

(71) Applicant: Arizona Board of Regents on behalf of Arizona State University, Scottsdale, AZ (US)

(72) Inventors: Neal W. Woodbury, Tempe, AZ (US); Alexander T. Taguchi, Cambridge, MA (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1269 days.

(21) Appl. No.: 17/427,786

(22) PCT Filed: Feb. 11, 2020

(86) PCT No.: PCT/US2020/017798
§ 371 (c)(1),
(2) Date: Aug. 2, 2021

(87) PCT Pub. No.: WO2020/167872
PCT Pub. Date: Aug. 20, 2020

(65) Prior Publication Data
US 2022/0130494 A1     Apr. 28, 2022

Related U.S. Application Data

(60) Provisional application No. 62/804,029, filed on Feb. 11, 2019.

(51) Int. Cl.
| | | |
|---|---|---|
| *G01N 33/48* | (2006.01) | |
| *G16B 40/10* | (2019.01) | |
| *G16B 40/20* | (2019.01) | |
| *G16C 20/50* | (2019.01) | |

(52) U.S. Cl.
CPC ............. G16C 20/50 (2019.02); G16B 40/10 (2019.02); G16B 40/20 (2019.02)

(58) Field of Classification Search
None
See application file for complete search history.

(56) References Cited

U.S. PATENT DOCUMENTS

| | | |
|---|---|---|
| 5,434,796 A | 7/1995 | Weininger |
| 2006/0206269 A1 | 9/2006 | Diller et al. |
| 2012/0065123 A1 | 3/2012 | Johnston et al. |
| 2015/0278441 A1 | 10/2015 | Min et al. |
| 2016/0176951 A1 | 6/2016 | Barelle et al. |
| 2017/0161635 A1 | 6/2017 | Oono et al. |

OTHER PUBLICATIONS

Aditya et al., DeepIU: An Architecture for Image Understanding, Advances in Cognitive Systems 4, 2016, 16 pages.
Aditya et al., Answering Image Riddles using Vision and Reasoning through Probabilistic Soft Logic, arXiv:1611.05896v1 [cs.CV], Nov. 17, 2016, 14 pages.
Aditya et al., Explicit Reasoning over End-to-End Neural Architectures for Visual Question Answering, The Thirty-Second AAAI Conference on Artificial Intelligence (AAAI-18), pp. 629-637.
Alikhani et al., Arrows are the Verbs of Diagrams, Proceeding of the 27th International Conference on Computational Linguistics, Aug. 20-26, 2018, pp. 3552-3563.
Alquraishi, End-to-End Differentiable Learning of Protein Structure, Cell Systems 8, Apr. 24, 2019, pp. 292-301.
Amanchy et al., Stable Isotope Labeling with Amino Acids in Cell Culture (SILAC) for Studying Dynamics of Protein Abundance and Posttranslational Modifications, Science's stke, Protocol, Jan. 18, 2005, 20 pages.
Belkin et al., Laplacian Eigenmaps for Dimensionality Reduction and Data Representation, Neural Computation, 15, 2003, pp. 1373-1396.
Berisha et al., Empirically Estimable Classification Bounds Based on a Nonparametric Divergence Measure, IEEE Transactions on Signal Processing, vol. 64, No. 3, Feb. 1, 2016, pp. 580-591.
Choudhury et al., Automatic Extraction of Figures from Scholarly Documents, DocEng '15, Sep. 8-11, 2015, pp. 47-50.
Choudhury et al., An Architecture for Information Extraction from Figures in Digital Libraries, WWWWW 2015 Companion, May 18-22, 2015, pp. 667-672.
Clark et al., PDFFigures 2.0: Mining Figures from Research Papers, JCDL '16, Jun. 19-23, 2016 pp. 143-152.
Seo et al., Diagram Understanding in Geometry Questions, Proceeding of the Twenty-Eighth AAAI Conference on Artificial Intelligence, 2014, pp. 2831-2838.
Dimaio et al., Modeling Symmetric Macromolecular Structures in Rosetta3, PLoS One, vol. 6, Issue 6, Jun. 2011, 13 pages.
Evans et al., De novo structure prediction with deep-learning based scoring, ResearchGate, Dec. 2018, 3 pages.
Clark et al., Looking Beyond Text: Extracting Figures, Tables, and Captions from Computer Science Papers, Scholarly Big Data: AI Perspectives, Challenges, and Ideas: Papers from the 2015 AAAI Workshop, 7 pages.

(Continued)

*Primary Examiner* — Anna Skibinsky
(74) *Attorney, Agent, or Firm* — MH2 Technology Law Group LLP

(57)     ABSTRACT

Mechanisms for molecule design using machine learning include: forming a first training set for a neural network using, for each of a first plurality of known molecules, a plurality of input values that represent the structure of the known molecule and a plurality of functional property values for the known molecule; training the neural network using the first training set; proposing a first plurality of proposed molecules, and predicting first predicted functional property values of the first plurality of proposed molecules that have the desired function property values; causing the first plurality of proposed molecules to be synthesized to form a first plurality of synthesized molecules; receiving first measured functional property values of the first plurality of synthesized molecules; and adding data regarding the first plurality of synthesized molecules to the first training set to form a second training set and retrain the neural network using the second training set.

27 Claims, 39 Drawing Sheets

(56)                    References Cited

OTHER PUBLICATIONS

Fout et al., Protein Interface Prediction using Graph Convolutional Networks, 31st Conference on Neural Information Processing Systems (NIPS 2017), 10 pages.

Gao et al., Destini: A deep-learning approach to contact-driven protein structure prediction, Scientific Reports, 9:3514, 2019, 13 pages.

Gfeller et al., SwissSidechain: a molecular and structural database of non-natural sidechains, Nucleic Acids Research, 2013, vol. 41, Oct. 26, 2012, Database issue pp. D327-D332.

Ghodsi, Dimensionality Reduction A Short Tutorial, Department of Statistics and Actuarial Science University of Waterloo, 2006, 25 pages.

Grover et al., Flow-GAN: Bridging implicit and prescribed learning in generative models, ResearchGate, May 2017, 7 pages.

Guye et al., Genetically engineering self-organization of human pluripotent stem cells into a liver bud-like tissue using Gata6, Nature Communications, 7:10243, 12 pages.

Haney et al., Reassessing the Host Defense Peptide Landscape, Frontiers in Chemistry, vol. 7, Article 43, Feb. 2019, 22 pages.

Hashemifar et al., Predicting protein-protein interactions through sequence-based deep learning, Bioinformatics, 34, 2018, pp. i802-i810.

Hobbs et al., Toward a Formal Theory of Information Structure, USC Information Sciences Institute, 25 pages.

Ioffe et al., Batch Normalization: Accelerating Deep Network Training by Reducing Internal Covariate Shift, Google, 1600 Amphitheatre Pkwy, Mountain View, CA 94043, 9 pages.

Jain et al., Low-rank Matrix Completion using Alternating Minimization, STOC '13, Jun. 1-4, 2013, pp. 665-674.

Jenson et al., Peptide design by optimization on a data-parameterized protein interaction landscape, PNAS, vol. 115, No. 44, pp. E10342-E10351.

Jespersen et al., Antibody Specific B-Cell Epitope Predictions: Leveraging Information From Antibody-Antigen Protein Complexes, Frontiers in Immunology, vol. 10, Article 298, Feb. 2019, 10 pages.

Johansson-Akhe, et al., Predicting protein-peptide interaction sites using distant protein complexes as structural templates, Scientific Reports, 9:4267, 2019, 13 pages.

Kembhavi et al., A Diagram is Worth a Dozen Images, ECCV, Part IV, LNCS 9908, 2016, pp. 235-251.

Konyk et al., Chemical Knowledge for the Semantic Web, ResearchGate, Jun. 2008, 9 pages.

Kurata et al., Structure and Semantics of Arrow Diagrams, COSIT, LNCS 3693, 2005, pp. 232-250.

Legutki et al., Scalable high-density peptide arrays for comprehensive health monitoring, Nature Communications, 5:4785, 2014, 7 pages.

Liang et al., An Index for Characterization of Natural and Non-Natural Amino Acids for Peptidomimetics, PLoS One, vol. 8, Issue 7, e67844, Jul. 2013, 16 pages.

Liu et al., Antibody complementarity determining region design using high-capacity machine learning, Bioinformatics, 36(7), 2020, pp. 2126-2133.

Lee et al., Machine learning-enabled discovery and design of membrane-active peptides, Bioorg Med Chem., 26(10), Jun. 1, 2018, pp. 2708-2718.

Mayne et al., Rapid parameterization of small molecules using the Force Field Toolkit, J Comput Chem., 34(32), Dec. 15, 2013, 28 pages.

Miao et al., Gaussian Accelerated Molecular Dynamics: Unconstrained Enhanced Sampling and Free Energy Calculation, Journal of Chemical Theory and Computation, 11, 2015, pp. 3584-3595.

Nair et al., Rectified Linear Units Improve Restricted Boltzmann Machines, Proceedings of the 27th International Conference on Machine Learning, Israel, 2010, 8 pages.

Rose et al., The new biology: beyond the Modern Synthesis, Biology Direct, 2:30, Nov. 24, 2007, 17 pages.

Rowe et al., An ImmunoSignature test distinguishes Trypanosoma cruzi, hepatitis B, hepatitis C and West Nile virus seropositivity among asymptomatic blood donors, PLOS Neglected Tropical Diseases, Sep. 5, 2017, 30 pages.

Ruder, An overview of gradient descent optimization algorithms*, arXiv:1609.04747v1 [cs.LG], Sep. 15, 2016, 12 pages.

Sandberg, log, 1998, 1 page.

Savva et al., ReVision: Automated Classification, Analysis and Redesign of Chart Images, Paper Session: Patterns, UIST'11, Oct. 16-19, 2011, 10 pages.

Schirrmeister et al., Training Generative Reversible Networks, Presented at the ICML 2018 workshop on Theoretical Foundations and Applications of Deep Generative Models, Stockholm, Sweden, PMLR 80, 2018, 10 pages.

Siegel et al., FigureSeer: Parsing Result-Figures in Research Papers, Allen Institute for Artificial Intelligence, University of Washington, http://allenai.org/plato/figureseer, 16 pages.

Singh et al., Humoral Immunity Profiling of Subjects with Myalgic Encephalomyelitis Using a Random Peptide Microarray Differentiates Cases from Controls with High Specificity and Sensitivity, Mol Neurobiol, 55, 2018, pp. 633-641.

Srivastava et al., Dropout: A Simple Way to Prevent Neural Networks from Overfitting, Journal of Machine Learning Research 15, 2014, pp. 1929-1958.

Tallorin et al., Discovering de novo peptide substrates for enzymes using machine learning, Nature Communications, 9:5253, 2018, 10 pages.

Tominaga, Comparative study of class data analysis with PCA-LDA, SIMCA, PLS, ANNs, and k-NN, Chemometrics and Intelligent Laboratory Systems, 49, 1999, pp. 105-115.

Sharma et al., Towards Addressing the Winograd Schema Challenge—Building and Using a Semantic Parser and a Knowledge Hunting Module, Proceedings of the Twenty-Fourth International Joint Conference on Artificial Intelligence, 2015, pp. 1319-1325.

Tu et al., Objective Assessment of Pathological Speech Using Distribution Regression, IEEE, ICASSP, 2017, pp. 5050-5054.

Udell et al., Generalized Low Rank Models, Foundations and Trends in Machine Learning, vol. 9, No. 1, 2016, pp. 1-118.

Valenzuela-Escarcega et al., Large-scale automated machine reading discovers new cancer-driving mechanisms, Database, 2018, pp. 1-14.

Vanommeslaeghe et al., Automation of the CHARMM General Force Field (CGenFF) I: Bond Perception and Atom Typing, Journal of Chemical Information and Modeling, 52, 2012, pp. 3144-3154.

Velazquez et al., Programming Morphogenesis through Systems and Synthetic Biology, Trends in Biotechnology, vol. 36, No. 4, Apr. 2018, pp. 415-429.

Veltri et al., Deep learning improves antimicrobial peptide recognition, Bioinformatics, 34(16), 2018, pp. 2740-2747.

Vo et al., The NL2KR Platform for building Natural Language Translation Systems, Proceedings of the 53rd Annual Meeting of the Association for Computational Linguistics and the 7th International Joint Conference on Natural Language Processing, Bejing, China, Jul. 26-31, 2015, pp. 899-908.

Wang, Closed-form Inverse Kinematic Solution for Anthropomorphic Motion in Redundant Robot Arms, A Thesis Presented in Partial Fulfillment of the Requirements for the Degree Master of Science, Arizona State University, 2013, 54 pages.

Warren et al., On the Control of Human-Robot Bi-Manual Manipulation, J Intell Robot Syst, 78, 2015, pp. 21-32.

Williams et al., Creating Protein Affinity Reagents by Combining Peptide Ligands on Synthetic DNA Scaffolds, J. Am. Chem. Soc., 131, 2009, pp. 17233-17241.

Wisler et al., Empirically-Estimable Multi-Class Classification Bounds, IEEE, ICAASP, 2016, pp. 2594-2598.

Wisler et al., A data-driven basis for direct estimation of functionals of distributions, arXiv:1702.06516v1 [cs.IT], Feb. 21, 2017, 13 pages.

Wisler et al., Direct Estimation of Density Functionals Using a Polynomial Basis, IEEE Transactions on Signal Processing, vol. 66, No. 3, Feb. 1, 2018, pp. 558-572.

(56)                    References Cited

OTHER PUBLICATIONS

Yang et al., Corpus-Guided Sentence Generation of Natural Images, Proceedings of the 2011 Conference on Empirical Methods in Natural Language Processing, Edinburgh, Scotland, UK, Jul. 27-31, 2011,pp. 444-454.
Yang et al., A Cognitive System for Understanding Human Manipulation Actions, Advances in Cognitive Systems, 3, 2014, pp. 67-86.
Yoshida et al., Using Evolutionary Algorithms and Machine Learning to Explore Sequence Space for the Discovery of Antimicrobial Peptides, Chem 4, Mar. 8, 2018, pp. 533-543.

# of Features Used

1000

| Protein | Corr. Coef. |
|---|---|
| Diaphorase | 0.985 ± 0.001 |
| Ferredoxin | 0.983 ± 0.001 |
| FNR | 0.994 ± 0.001 |
| PD1 | 0.959 ± 0.002 |
| PDL1 | 0.965 ± 0.003 |
| TNFα | 0.960 ± 0.002 |
| TNFα Receptor | 0.973 ± 0.001 |
| Transferrin | 0.979 ± 0.001 |
| Fc | 0.924 ± 0.007 |

FIG. 12

Amino Acid

|  | | A | D | E | F | G | H | K | L | N | P | Q | R | S | V | W | Y |
|---|---|---|---|---|---|---|---|---|---|---|---|---|---|---|---|---|---|
| Sequence Position | 1 | 0 | 0 | 1 | 0 | 0 | 0 | 0 | 0 | 0 | 0 | 0 | 0 | 0 | 0 | 0 | 0 |
| | 2 | 0 | 0 | 0 | 0 | 0 | 0 | 0 | 0 | 0 | 0 | 1 | 0 | 0 | 0 | 0 | 0 |
| | 3 | 0 | 0 | 0 | 0 | 0 | 0 | 0 | 0 | 1 | 0 | 0 | 0 | 0 | 0 | 0 | 0 |
| | 4 | 0 | 0 | 0 | 0 | 0 | 0 | 0 | 0 | 0 | 0 | 0 | 0 | 1 | 0 | 0 | 0 |
| | 5 | 0 | 0 | 0 | 0 | 0 | 0 | 0 | 0 | 0 | 0 | 1 | 0 | 0 | 0 | 0 | 0 |
| | 6 | 0 | 0 | 0 | 0 | 0 | 0 | 0 | 0 | 0 | 0 | 0 | 0 | 0 | 1 | 0 | 0 |
| | 7 | 0 | 1 | 0 | 0 | 0 | 0 | 0 | 0 | 0 | 0 | 0 | 0 | 0 | 0 | 0 | 0 |
| | 8 | 0 | 0 | 0 | 0 | 1 | 0 | 0 | 0 | 0 | 0 | 0 | 0 | 0 | 0 | 0 | 0 |
| | 9 | 0 | 0 | 0 | 0 | 0 | 0 | 0 | 0 | 0 | 0 | 0 | 0 | 0 | 0 | 0 | 0 |
| | 10 | 0 | 0 | 0 | 0 | 0 | 0 | 0 | 0 | 0 | 0 | 0 | 0 | 0 | 0 | 0 | 0 |
| | 11 | 0 | 0 | 0 | 0 | 0 | 0 | 0 | 0 | 0 | 0 | 0 | 0 | 0 | 0 | 0 | 0 |
| | 12 | 0 | 0 | 0 | 0 | 0 | 0 | 0 | 0 | 0 | 0 | 0 | 0 | 0 | 0 | 0 | 0 |
| | 13 | 0 | 0 | 0 | 0 | 0 | 0 | 0 | 0 | 0 | 0 | 0 | 0 | 0 | 0 | 0 | 0 |

FIG. 23

Chemical Space

| Sequence Position | | | | | |
|---|---|---|---|---|---|
| 1 | -0.530 | 2.268 | 0.715 | 0.852 | -0.268 |
| 2 | -0.551 | -1.228 | -0.432 | 2.422 | -0.003 |
| 3 | -0.160 | 0.859 | 0.214 | -0.944 | 0.309 |
| 4 | -0.232 | -0.505 | -1.274 | 1.842 | -0.110 |
| 5 | -0.551 | -1.228 | -0.432 | 2.422 | -0.003 |
| 6 | 1.423 | -0.716 | -0.430 | -0.004 | 0.924 |
| 7 | -1.353 | -0.801 | -0.864 | -0.028 | -0.247 |
| 8 | -2.251 | -0.413 | -0.504 | -0.237 | 1.036 |
| 9 | 0.000 | 0.000 | 0.000 | 0.000 | 0.000 |
| 10 | 0.000 | 0.000 | 0.000 | 0.000 | 0.000 |
| 11 | 0.000 | 0.000 | 0.000 | 0.000 | 0.000 |
| 12 | 0.000 | 0.000 | 0.000 | 0.000 | 0.000 |
| 13 | 0.000 | 0.000 | 0.000 | 0.000 | 0.000 |

FIG. 24

SYSTEMS, METHODS, AND MEDIA FOR MOLECULE DESIGN USING MACHINE LEARNING MECHANISMS

CROSS-REFERENCE TO RELATED APPLICATION

This application claims the benefit of U.S. Provisional Patent Application No. 62/804,029, filed Feb. 11, 2019, which is hereby incorporated by reference herein in its entirety.

STATEMENT REGARDING GOVERNMENT FUNDED RESEARCH

This invention was made with government support under Grant No. HSHQDC-15-C-B0008 awarded by the Department of Homeland Security. The government has certain rights in the invention.

BACKGROUND

The rapid creation of new, functionally specific molecules is essential to a large range of biomedical applications. Of particular interest are molecules that bind to specific targets such as receptors, enzymes, aggregates, hormones, pathogens, diseased cells, etc. and either act to change the activity of the target or simply to serve as part of a detection scheme. Such molecules can be therapeutics, vaccines or part of a diagnostic. Past approaches to developing new molecules have either relied on rational design, which is limited by the personal knowledge of the chemist involved, or have relied on luck, sparsely sampling immense structure/function spaces and only selecting for one or two functional dimensions when many different functional parameters are critical. In either case, the result is at best a lead compound optimized towards a local maximum.

Accordingly, new mechanisms for molecule design are desirable.

SUMMARY

System, method, and media for molecule design using machine learning mechanisms are provided. In some embodiments, systems for proposing molecules having desired functional property values are provided. These systems include a memory and a hardware processor that is coupled to the memory. The hardware processor is configured to form a first training set for a neural network using, for each of a first plurality of known molecules, a plurality of input values that represent the structure of the known molecule and a plurality of functional property values for the known molecule. The hardware processor is then configured to train the neural network using the first training set. The hardware processor is next configured to propose a first plurality of proposed molecules, and predict first predicted functional property values of the first plurality of proposed molecules that have the desired function property values. The hardware processor is then configured to cause the first plurality of proposed molecules to be synthesized to form a first plurality of synthesized molecules. The hardware processor is next configured to receive first measured functional property values of the first plurality of synthesized molecules. The hardware processor is then configured to add data regarding the first plurality of synthesized molecules to the first training set to form a second training set and retrain the neural network using the second training set.

In some implementations of the system, the plurality of input values for each of the first plurality of known molecules are based on one-hot representations of building block molecules that form the known molecule.

In some implementations of the system, the building block molecules are amino acids.

In some implementations of the system, the known molecules are peptides.

In some implementations of the system, the plurality of input values for each of the first plurality of known molecules are based on chemical properties of building block molecules that form the known molecule.

In some implementations of the system, the neural network includes an encoder layer based on chemical properties of building block molecules that form the first plurality of known molecules.

In some implementations of the system, an iterative process is used to propose the first plurality of proposed molecules. In some implementations of the system, the iterative process attempts to find a local maximum based on each of the first plurality of proposed molecules.

In some implementations of the system, the hardware processor is further configured to: propose a second plurality of proposed molecules, and predict second predicted functional property values of the second plurality of proposed molecules that have the desired function property values; cause the second plurality of proposed molecules to be synthesized to form a second plurality of synthesized molecules; receive second measured functional property values of the second plurality of synthesized molecules; and determine whether the second measured functional property values a threshold amount different from the first measured functional property values.

In some embodiments, methods for proposing molecules having desired functional property values are provided. The methods form a first training set for a neural network using, for each of a first plurality of known molecules, a plurality of input values that represent the structure of the known molecule and a plurality of functional property values for the known molecule. Next, the methods train the neural network using the first training set using a hardware processor. The methods then propose a first plurality of proposed molecules, and predict first predicted functional property values of the first plurality of proposed molecules that have the desired function property values. Next, the methods cause the first plurality of proposed molecules to be synthesized to form a first plurality of synthesized molecules. Then, the methods receive first measured functional property values of the first plurality of synthesized molecules. Next, the methods add data regarding the first plurality of synthesized molecules to the first training set to form a second training set and retrain the neural network using the second training set.

In some implementations of the methods, the plurality of input values for each of the first plurality of known molecules are based on one-hot representations of building block molecules that form the known molecule.

In some implementations of the methods, the building block molecules are amino acids.

In some implementations of the methods, the known molecules are peptides.

In some implementations of the methods, the plurality of input values for each of the first plurality of known molecules are based on chemical properties of building block molecules that form the known molecule.

In some implementations of the methods, the neural network includes an encoder layer based on chemical properties of building block molecules that form the first plurality of known molecules.

In some implementations of the methods, an iterative process is used to propose the first plurality of proposed molecules. In some implementations of the methods, the iterative process attempts to find a local maximum based on each of the first plurality of proposed molecules.

In some implementations of the methods, the methods also: propose a second plurality of proposed molecules, and predict second predicted functional property values of the second plurality of proposed molecules that have the desired function property values; cause the second plurality of proposed molecules to be synthesized to form a second plurality of synthesized molecules; receive second measured functional property values of the second plurality of synthesized molecules; and determine whether the second measured functional property values a threshold amount different from the first measured functional property values.

In some embodiments, non-transitory computer-readable media containing computer executable instructions that, when executed by a processor, cause the processor to perform a method proposing molecules having desired functional property values are provided. In these non-transitory computer-readable media, the method includes forming a first training set for a neural network using, for each of a first plurality of known molecules, a plurality of input values that represent the structure of the known molecule and a plurality of functional property values for the known molecule. The method also includes training the neural network using the first training set. The method further includes proposing a first plurality of proposed molecules, and predicting first predicted functional property values of the first plurality of proposed molecules that have the desired function property values. The method also includes causing the first plurality of proposed molecules to be synthesized to form a first plurality of synthesized molecules. The method further includes receiving first measured functional property values of the first plurality of synthesized molecules. And the method includes adding data regarding the first plurality of synthesized molecules to the first training set to form a second training set and retrain the neural network using the second training set.

In some implementations of the non-transitory computer-readable media, the plurality of input values for each of the first plurality of known molecules are based on one-hot representations of building block molecules that form the known molecule.

In some implementations of the non-transitory computer-readable media, the building block molecules are amino acids.

In some implementations of the non-transitory computer-readable media, the known molecules are peptides.

In some implementations of the non-transitory computer-readable media, the plurality of input values for each of the first plurality of known molecules are based on chemical properties of building block molecules that form the known molecule.

In some implementations of the non-transitory computer-readable media, the neural network includes an encoder layer based on chemical properties of building block molecules that form the first plurality of known molecules.

In some implementations of the non-transitory computer-readable media, an iterative process is used to propose the first plurality of proposed molecules. In some implementations of the non-transitory computer-readable media, the iterative process attempts to find a local maximum based on each of the first plurality of proposed molecules.

In some implementations of the non-transitory computer-readable media, the method further includes: proposing a second plurality of proposed molecules, and predicting second predicted functional property values of the second plurality of proposed molecules that have the desired function property values; causing the second plurality of proposed molecules to be synthesized to form a second plurality of synthesized molecules; receiving second measured functional property values of the second plurality of synthesized molecules; and determining whether the second measured functional property values a threshold amount different from the first measured functional property values.

BRIEF DESCRIPTION OF THE DRAWINGS

FIG. 12 is an example of a list of proteins that can be used in accordance with some embodiments.

FIG. 23 is an example of a sparse binary matrix representation of peptides (EQNSQVDG shown as an example) in accordance with some embodiments.

FIG. 24 is an example of a dense matrix representation of peptides (EQNSQVDG shown as an example) in accordance with some embodiments.

DETAILED DESCRIPTION

Figure 1A:
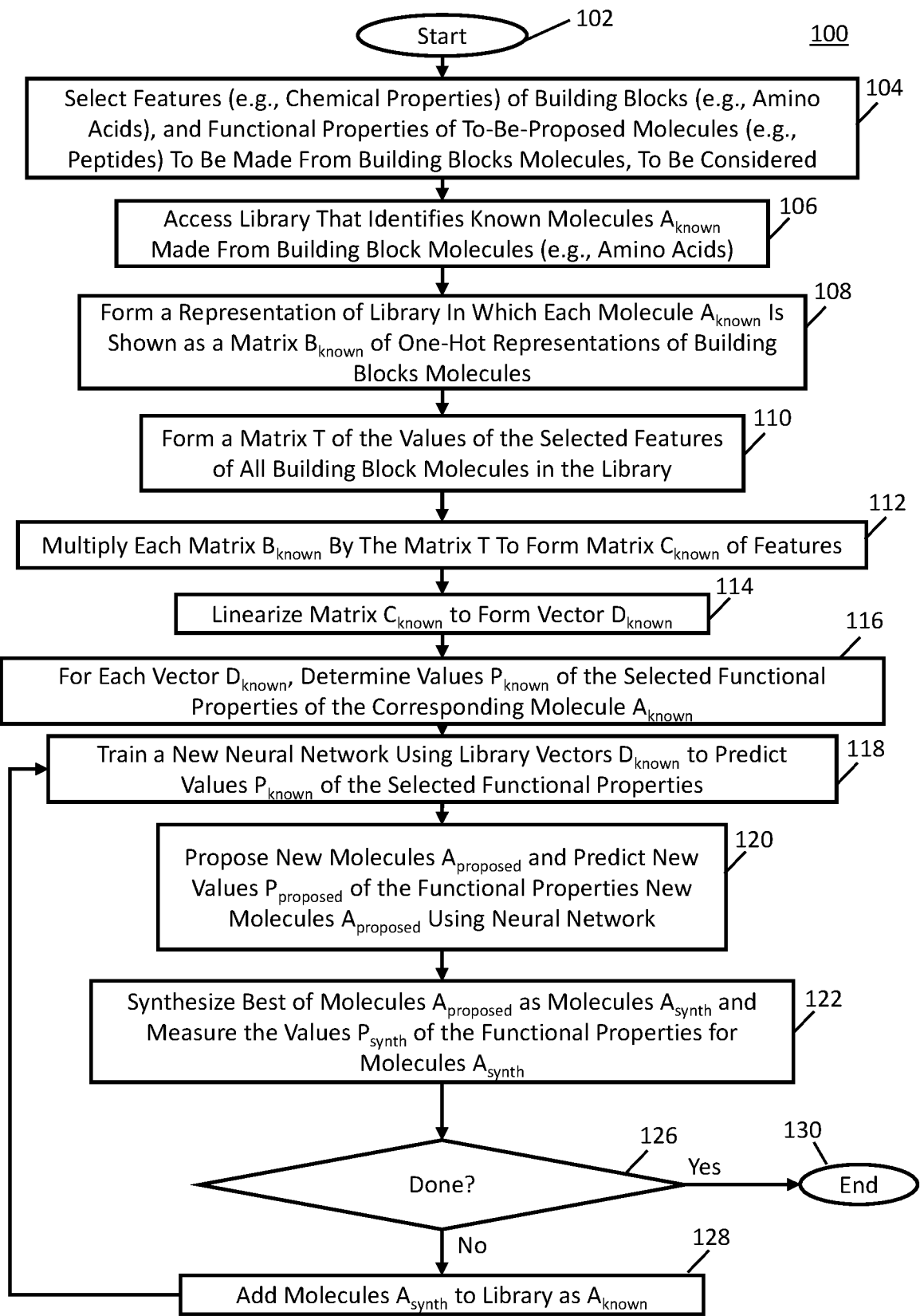
FIG. 1A is an example of a process for training a neural network to predict functional properties of proposed molecules (e.g., peptides) made from building block molecules (e.g., amino acids) in accordance with some embodiments.

In accordance with some embodiments, new mechanisms (which can include system, methods, and/or media) for molecule design are provided.

In some embodiments, the mechanisms can be thought of as solving the following equation:

$$\vec{F} = f(\vec{s})$$

This equation can be solved for the relationship $f$, where $\vec{F}$ is a desired set of measurable molecular functions (target binding, stability, etc.) of a to-be-designed molecule and $\vec{s}$ is a set of parameters that defines the structure of building block molecules (the sequence of building block molecules linked together) to be used to build the to-be-designed molecule.

In some embodiments, an abstract chemical space (e.g., including the building block molecules alanine, valine, and serine) is converted into sets of chemical/physical properties or combinations thereof (strings of real numbers). By describing the function $f$ as operating on chemical/physical properties of building block molecules a continuous, real-valued space can be defined as the input to the function $f$.

In some embodiments, the mechanisms can be used to design molecules that can be created by attaching building block molecules using chemistries amenable to solid phase synthesis on commercial synthesizers. Then, in some embodiments, a molecule designed by these mechanisms can be made by a single synthesizer that can be remotely programmed making the desired molecules on-site. For example, desired molecules can be created by attaching building block molecules via amide bonds, ester bonds, click chemistry and others using solid phase synthesis.

In some embodiments, mechanisms described herein can be used to design molecules in a large chemical space. For example, this space can include peptides with lengths between about 7 and 11 residues made from 16 of the natural amino acids (ADEFGHKLNPQRSVWY). There are $>10^{12}$ possible sequences in this chemical space. $\sim 10^5$ of these sequences can be selected in a nearly random fashion and synthesized on a peptide array to provide a training set of known molecules for a neural network (or another suitable machine learning mechanism). Array synthesis can be performed in any suitable manner, such as by using the techniques described in Legutki J B, Zhao Z G, Greying M, Woodbury N, Johnston S A, Stafford P, "Scalable High-Density Peptide Arrays for Comprehensive Health Monitoring," Nat Commun. 2014; 5:4785, which is hereby incorporated by reference herein in its entirety. A purified target protein can then be fluorescently labeled and incubated with the array, generating a pattern of binding that can be used to describe the functional properties of the known molecules in the training set.

In some embodiments, a neural network (or another suitable machine learning mechanism) can then be used to model the known molecules and their functional properties, such as the binding interactions between the peptides on the array and their target. In some embodiments, the neural network can be implemented in any suitable manner. For example, in some embodiments, the neural network can be implemented in PyTorch™ available from pytorch.org. As another example, in some embodiments, the neural network can have any suitable number of hidden layers (e.g., two), any suitable number of nodes per layer (e.g., 100), and can use any suitable activation function (e.g., ReLU).

Turning to FIG. 1A, an example 100 of a process for training a neural network to predict functional properties of proposed molecules (e.g., peptides) made from building block molecules (e.g., amino acids) in accordance with some embodiments is shown. Any suitable molecules can be proposed in some embodiments. For example, in some embodiments, the proposed molecules can be peptides, peptoides, nucleic acids, peptide nucleic acid polymers, polysaccharides, ester-linked polymers, amide-lined polymers, ether-linked polymers and/or any other suitable molecules made by covalently coupling multiple building block molecules together. Any suitable building block molecules can be used in some embodiments. For example, in some embodiments, the building block molecules can be amino acids, nucleic acids, peptide nucleic acids, sugars, and/or any other suitable building block molecules with distinct groups appropriate for coupling to other building block molecules (alcohols, alkynes, aldehydes, ketones, alkenes, etc.). The proposed molecules can be made from the building block molecules in any suitable manner in some embodiments. For example, in some embodiments, the proposed molecules can be made from the building block molecules by the building block molecules being linked together in a chain, a circle, a branched structure, and/or in any other suitable manner.

As illustrated, after process 100 begins at 102, the process, at 104, selects features (e.g., chemical properties) of building block molecules, and functional properties of to-be-proposed molecules to be made from the building block molecules to be considered by a machine learning mechanism, such as a neural network.

Any suitable features of the building block molecules, and any suitable number of features, can be selected, and the features can be selected in any suitable manner in some embodiments. For example, in some embodiments, when the building block molecules are amino acids, the features can be: molecular weight between 75 and 250; high amide coupling yield; appropriate protecting molecules; diverse side chain volume; diverse hydrophobicity; diverse accessible surface area (polar/nonpolar); stability in air, buffer, serum; diverse redox potential (when appropriate); diverse number of hydrogen bond donors and acceptors; low toxicity; diverse isoelectric point; moderate to high solubility (water, acetonitrile); diverse IR spectrum; few/nontoxic breakdown products; diverse pKa (when appropriate); and/or any other suitable chemical features. More particularly, in some embodiments, the features can be the isoelectric point and hydrophobicity of the building block molecules. As another example, in some embodiments, twelve, or any other suitable number of, features can be selected. As still another example, in some embodiments, the features can be selected by receiving selections from a user via a user interface, a configuration file, or any other suitable input mechanism.

Any suitable functional properties of the to-be-proposed molecules to be made from the building block molecules can be selected, any suitable number of functional properties can be selected, and the functional properties can be selected in any suitable manner. For example, in some embodiments, when the to-be-proposed molecules are peptides, the functional features can be: binding to a particular target; binding to things that are off target; binding constants; binding rates; reactivity to specific chemicals; rate of degradation (e.g., in blood); rate of clearance by the liver and kidneys; ability to cross into a cell (in general, target accessibility); solubility of the molecule in blood or appropriate solution; catalytic properties; inhibition/activation of enzyme activity by the molecule; toxicity of the molecule (e.g., toxicity to a cancer cell or bacterium might be good, but toxicity to a normal cell might be bad); inhibition/activation of receptor activity by the molecule; and/or any other suitable functional properties. As another example, in some embodiments, twelve, or any other suitable number of, functional properties can be selected. As still another example, in some embodiments, the functional properties can be selected by receiving selections from a user via a user interface, a configuration file, or any other suitable input mechanism.

Next, at 106, a library that identifies known molecules $A_{known}$ made from building block molecules can be accessed. This library can be accessed from any suitable source in any suitable manner in some embodiments. For example, the library can be accessed from a server via a communication network in some embodiments. The library can be stored in any suitable data structure, such as in a database, in some embodiments. The library can identify the known molecules $A_{known}$ made from building block molecules in any suitable manner. For example, in some embodiments, when the known molecules are peptides, the library can identify a sequence of the amino acids forming the peptides using letter codes for the amino acids. E.g., with a peptide formed from alanine (which is commonly represented by the letter code A), aspartic acid (which is commonly represented by the letter code D), glutamic acid (which is commonly represented by the letter code E), and alanine (which is commonly represented by the letter code A), the letters ADEA can be used.

While a library is described herein, it should be apparent that the library may be part of a larger library and the library need not be the entirety of an available larger library.

Then, at 108, process 100 can form a representation of the library in which each known molecule $A_{known}$ is shown as a matrix $B_{known}$ of one-hot representations of building block molecules (e.g., formed using one-hot encoding). The one-hot representations can be formed in any suitable manner, can have any suitable format, and can have any suitable length. For example, in some embodiments, when the building block molecules are amino acids, three amino acids are being considered, alanine is the first of the three amino acids, asparagine is the second of the three amino acids, and glutamic acid is the third of the three amino acids, a molecule A for amino acids ADEA can be represented by a matrix $B_{known}$ as:

| $B_{known}$ | A | D | E |
|---|---|---|---|
| $1^{st}$ position | 1 | 0 | 0 |
| $2^{nd}$ position | 0 | 1 | 0 |
| $3^{rd}$ position | 0 | 0 | 1 |
| $4^{th}$ position | 1 | 0 | 0 | wherein 1 0 0 is the one-hot representation for alanine, 0 1 0 is the one-hot representation for asparagine, and 0 0 1 is the one-hot representation for glutamic acid.

At 110, process 100 can form a matrix T of the values V of the selected features of all of the building block molecules in the library or all of the features of the building block molecules to be considered. For example, in some embodiments, assuming that three features were selected at 104, the features of amino acids A, D, and E can have values V of the selected features as follows:

| T | $1^{st}$ Feature | $2^{nd}$ Feature | $3^{rd}$ Feature |
|---|---|---|---|
| A | 1.1 | 3.2 | 1.8 |
| D | 2.7 | 4.0 | −0.4 |
| E | 2.2 | 4.2 | −0.8 |

Based on this and assuming that only amino acids A, D, and E are in the library, or only amino acids A, D, and E have been selected, at 110, process can form a matrix T as follows:

| | | |
|---|---|---|
| 1.1 | 2.7 | 2.2 |
| 3.2 | 4.0 | 4.2 |
| 1.8 | −0.4 | −0.8 |

Next, at 112, process 100 can multiply each matrix $B_{known}$ by the matrix T to form a matrix $C_{known}$ of features. For example, in some embodiments, continuing the above example, a matrix $C_{known}$ can be formed as follows:

| | | |
|---|---|---|
| 1.1 | 3.2 | 1.8 |
| 2.7 | 4.0 | −0.4 |
| 2.2 | 4.2 | −0.8 |
| 1.1 | 3.2 | 1.8 |

Then, at 114, process 100 can linearize each matrix $C_{known}$ to form vectors $D_{known}$. This can be performed in any suitable manner. For example, in some embodiments, continuing the example above for the values of matrix $C_{known}$, at 114, process can form a vector $D_{known}$ as follows:

1.1, 3.2, 1.8 2.7, 4.0, −0.4 2.2, 4.2, −0.8 1.1, 3.2, 1.8

At 116, process 100 can then, for each vector $D_{known}$, determine known values $P_{known}$ for corresponding known molecules of the functional properties selected at 104. These values can be determined in any suitable manner. For example, these values can be determined by looking-up previously measured values for corresponding known molecules in a database of measured values of known molecules (e.g., peptides) made from building block molecules (e.g., amino acids) or the values can be measured by synthesizing molecules and measuring their functional properties.

Next, at 118, process 100 can train a machine learning mechanism (e.g., such as a new neural network) using vectors $D_{known}$ to predict values $P_{known}$ of the selected function properties. The machine learning mechanism (e.g., neural network) can be trained in any suitable manner.

Then, at 120, process 100 can propose new molecules $A_{proposed}$ and predict values $P_{proposed}$ of the functional properties of the proposed molecules $A_{proposed}$ using the machine learning mechanism (e.g., neural network) trained at 118. The proposed molecules $A_{proposed}$ can have orders $O_{proposed}$ of building block molecules and specific identities of building block molecules $I_{proposed}$ at each position in the order. Process 100 can propose molecules $A_{proposed}$ in an attempt to increase the dynamic ranges of values of the selected functional properties over the corresponding values of known molecules in the library. Any suitable criteria or criterion can be used to determine whether the new values $P_{proposed}$, orders $O_{proposed}$, and identities $I_{proposed}$ increase the dynamic ranges of values of the selected functional properties in some embodiments.

The values $P_{proposed}$ of the functional properties of the proposed molecules $A_{proposed}$ can be predicted by forming vectors $D_{proposed}$ and then submitting each vector $D_{proposed}$ to the machine learning mechanism (e.g., neural network), which will then output $P_{proposed}$ for each vector $D_{proposed}$. $D_{proposed}$ can be created by: (1) forming one-hot representation $B_{proposed}$ of the proposed molecules $A_{proposed}$ (e.g., as described above in connection with 108); retrieving or creating a matrix T having values of the features of the building blocks molecules in the proposed molecules $A_{proposed}$ (e.g., as described above in connection with 110); multiplying $B_{proposed}$ by matrix T to form a matrix $C_{proposed}$ (e.g., as described above in connection with 112); and linearizing matrix $C_{proposed}$ to form a vector $D_{proposed}$ (e.g., as described above in connection with 114).

The proposed molecules $A_{proposed}$ can be selected in any suitable manner.

For example, in some embodiments, the proposed molecules $A_{proposed}$ can be selected by: (1) picking a large number of possible building block molecule orders and identities; (2) forming a vector $D_{proposed}$ for each $A_{proposed}$ (as described above); (3) entering $D_{proposed}$ into the machine learning mechanism (e.g., neural network); (4) receiving functional property value predictions $P_{proposed}$ from the output of the machine learning mechanism (e.g., neural network); (5) making small changes in the identity and/or order of the building block molecules in the proposed molecule $A_{proposed}$ around each initial selection of the identity and/or order of the building block molecules in the proposed molecule; (6) going back to (2) until all of the high peaks in $P_{proposed}$ in the vicinity of the initial selections have been identified; and (7) selecting as the proposed molecules $A_{proposed}$ the molecules corresponding to high peaks in $P_{proposed}$. In some embodiments, this approach can use a gradient ascent technique to find the high peaks in $P_{proposed}$ in the vicinity of the initial selections, and any suitable gradient ascent technique can be used. For example, in some embodiments, the Levenberg-Marquardt algorithm can be used as a gradient ascent technique.

As another example, in some embodiments, each possible combination and order of the available building block molecules can be used to form proposed molecules $A_{proposed}$. A vector $D_{proposed}$ for each $A_{proposed}$ can be computed (as described above) and entered into the machine learning mechanism (e.g., neural network) and functional property value predictions $P_{proposed}$ can be output from the machine learning mechanism (e.g., neural network) and stored. These functional property value predictions $P_{proposed}$ can then be searched to find the ones that most closely matches the desired functional properties.

As still another example, in some embodiments, the proposed molecules $A_{proposed}$ can be selected by using a reversible network as the machine learning mechanism, feeding the desired values of $P_{proposed}$ into the machine learning mechanism, obtaining values of $D_{proposed}$ from the machine learning mechanism, and searching for building block molecule combinations that match, or are closest to, $D_{proposed}$ to be used as proposed molecules $A_{proposed}$. Any suitable reversible network can be used as the machine learning mechanism in some implementations of these embodiments. For example, in some embodiments, a Generative Adversarial Network (GAN), a FlowGAN network (which is described in A. Grover, M. Dhar, S. Ermon, "Flow-GAN: Bridging implicit and prescribed learning in generative models," CoRR abs/1705.08868, (2017), which is hereby incorporated by reference herein in its entirety), or a reversible network (which is described in R. T. Schirrmeister, P. Chrabaszcz, F. Hutter, T. Ball, "Training Generative Reversible Networks.," arXiv:1806.01610v4 [cs.LG] (2018), which is hereby incorporated by reference herein in its entirety) can be used to as the machine learning mechanism.

At 122, process 100 can synthesize new the best performing ones of the proposed molecules $A_{proposed}$. Any suitable number of the best performing proposed molecules $A_{proposed}$ can by synthesized, and the proposed molecules $A_{proposed}$ can be synthesized in any suitable manner to form synthesized molecules $A_{synth}$. For example, in some embodiments, process 100 can instruct a computerized synthesizer (which can be any suitable computerized synthesizer, such as the Liberty Blue™ automated synthesizer available from CEM Corporation of Matthews, North Carolina) to synthesize the top 100 of proposed molecules $A_{proposed}$ to form synthesized molecules $A_{synth}$. Once molecules $A_{synth}$ have been formed, values $P_{synth}$ of the functional properties of synthesized molecules $A_{synth}$ can be determined in any suitable manner, in some embodiments. For example, in some embodiments, values $P_{synth}$ of the functional properties of synthesized molecules $A_{synth}$ molecules can be determined synthesizing the molecules $A_{synth}$ on beads and performing an assay function in solution or on the beads as known in the art.

Then, at 126, process 100 can determine whether the process is done. Process 100 can be determined as being done in any suitable manner.

For example, in some embodiments, process 100 can be determined as being done when the values $P_{synth}$ of the functional properties meet some threshold value (which can be any suitable value).

As another example, in some embodiments, process 100 can be determined as being done when the molecules proposed and/or synthesized over multiple (e.g., 2, 3, 4, 5, . . . ) iterations of the loop including 118, 120, 122, 126, and 128 do not appreciably improve (which can be determined by any suitable threshold). More particularly, for example, in some embodiments, process 100 can be determined as being done when synthesized molecules $A_{synth}$ show no appreciable improvement (which can be determined by any suitable threshold) in the values $P_{synth}$ of the functional properties over two or more iterations of the loop. As another more particular example, in some embodiments, process 100 can be determined as being done when the proposed molecules $A_{proposed}$ are the same after two or more consecutive loops.

Proposed molecules, synthesized molecules, function properties, vectors, training sets, and/or any other items discussed in connection with FIGS. 1A and 1B may be referred to as first, second, third, fourth, etc. to distinguish them from similar items from different iterations of the loop including 118, 120, 122, 126, and 128.

If process 100 is determined to be done at 126, then the molecule proposed (as $A_{proposed}$) and synthesized (as $A_{Synth}$) can be used for a desired purpose and process 100 can end at 130.

Otherwise, if process 100 is determined to be not done at 126, then process 100 can add the data for synthesized molecules $A_{synth}$ to the library and loop back to 118 to train a new neural network as described above. Any suitable data for synthesized molecules $A_{synth}$ can be added to the library, including but not limited to the order and identity of the building block molecules in $A_{synth}$, the vector $D_{synth}$ for synthesized molecules $A_{synth}$, and the measured values $P_{synth}$ of the functional properties for synthesized molecules $A_{synth}$.

Figure 2:
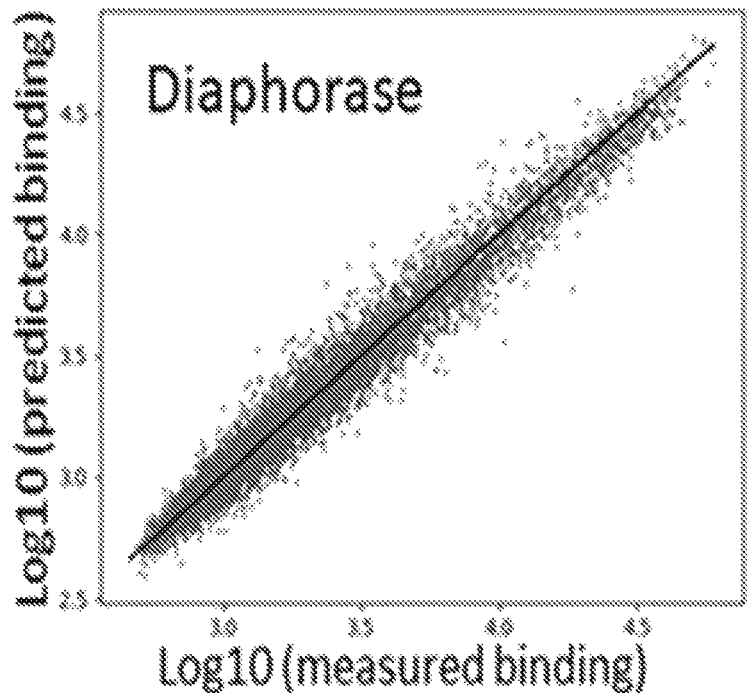
FIG. 2 is an example of a scatter plot of predicted values of a functional property (e.g., binding) as determined by a neural network versus measured values of the functional property (e.g., binding) for a simple, purified protein, fluorescently labeled diaphorase as the target (diaphorase is a dehydrogenase sometimes used in NADH or NADPH detection) in accordance with some embodiments.

FIG. 2 shows an example of a scatter plot of predicted values of a functional property (e.g., binding) as determined by a neural network trained as described above versus measured values of the functional property (e.g., binding) for a simple, purified protein, fluorescently labeled diaphorase as the target (diaphorase is a dehydrogenase sometimes used in NADH or NADPH detection). Binding values measured for 90% of peptides on an array (~113,000 peptides of the total 126,000 unique peptides on the array) were used to train the neural network (which had two hidden layers of width 100). The other 10% of peptides on the array (~13,000) where then used to test the neural network by using the neural network to predict the binding of those peptides. The data used was the average of three separate assays on three peptide arrays. The Pearson correlation coefficient between replicate runs was 0.99. The Pearson correlation coefficient between predicted and measured values was 0.98; the prediction is nearly as good as the measurement error of the data allows. Similar results have been obtained for eight other proteins (Ferredoxin, Ferredoxin NADP reductase, PD1 receptor, PDL1, TNF alpha, TNF alpha receptor, Transferrin).

Figure 3:
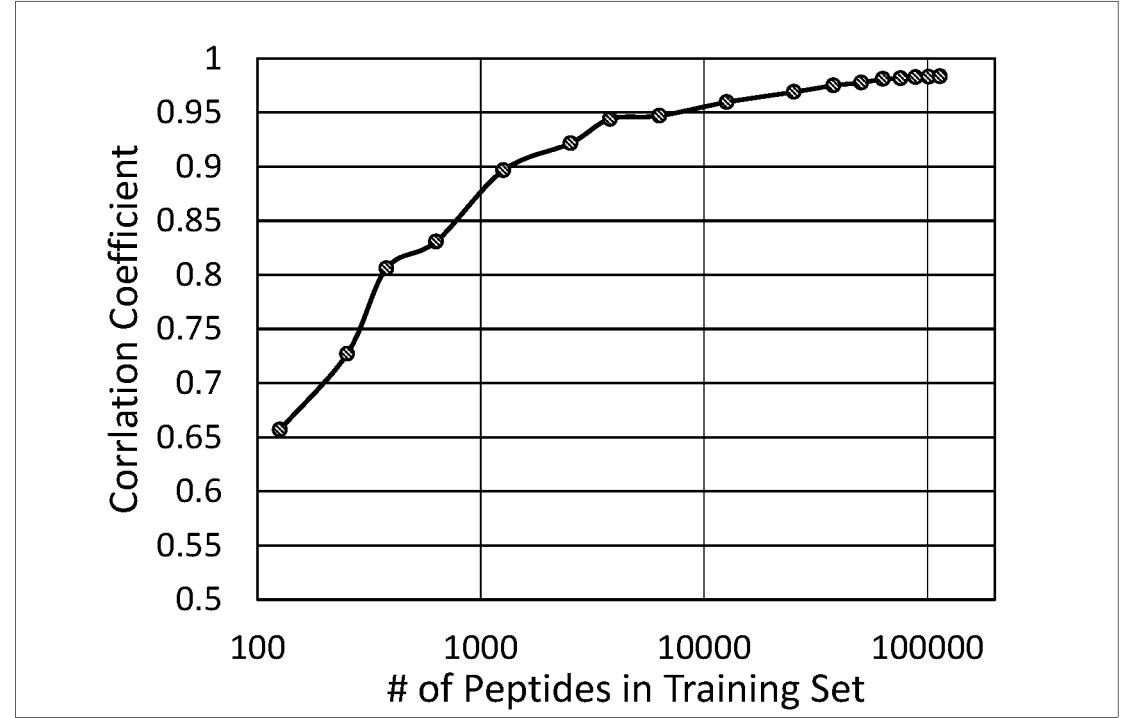
FIG. 3 is an example of how the accuracy of the neural network depends on the number of molecules (e.g., peptides) used in the training set in accordance with some embodiments.

FIG. 3 illustrates an example of how the accuracy of the neural network depends on the number of molecules (e.g., peptides) used in the training set. As shown, accuracy improves appreciably up to about 80,000 molecules and then reaches a point where it is likely limited by the measurement accuracy of the data. There is no benefit to increasing the width or number of hidden layers in the neural network. The implication of this result is that at least for the purified proteins measured, a very sparse sampling of $\sim10^5$ sequences is sufficient to describe the vast majority of the $\sim10^{12}$ possible sequences as well as the measurements allow. Even using just over $\sim10^3$ peptides in the training set gives a correlation coefficient of about 0.9, reinforcing the notion that sparse sampling can provide general models for prediction of binding.

While FIG. 1A describes a neural network that receives as its input a vector D that is a linearized form of the product (matrix C) of a matrix B and a matrix 2, in some embodiments, matrix B can be linearized to form a vector D and vector D can be used as an input to the neural network. In such case, an encoder layer having an encoder matrix T can be added to the neural network after the neural network's input layer to multiply the one-hot codes in vector D by values in the encoder matrix T. The neural network can then adjust the values in encoder matrix T as it learns based on training.

Figure 1B:
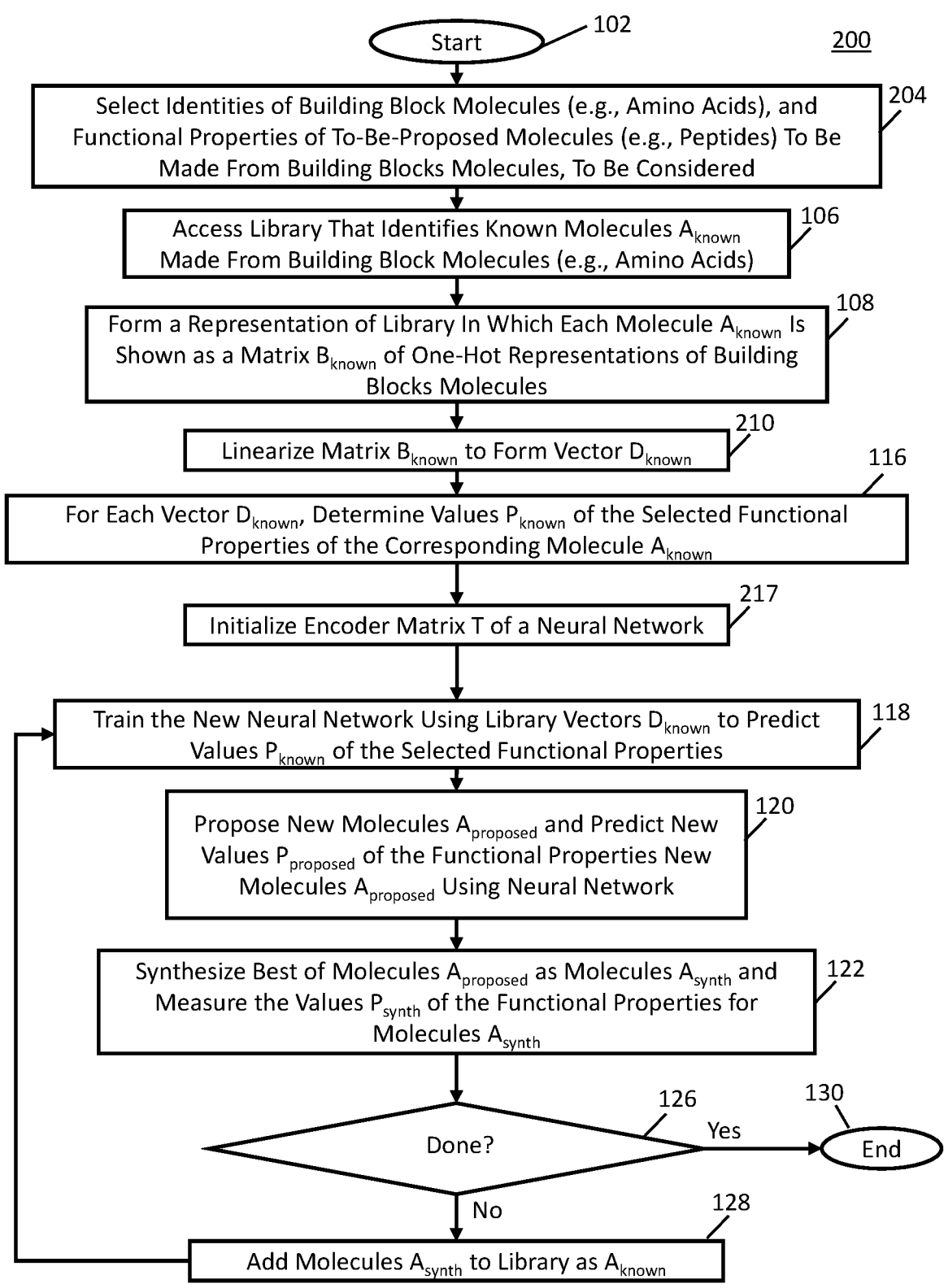
FIG. 1B is an example of a process for training a neural network to predict functional properties of proposed molecules (e.g., peptides) made from building block molecules (e.g., amino acids) in which an encoder matrix T is included in the neural network in accordance with some embodiments.

FIG. 1B is an example 200 of a process for training a neural network to predict functional properties of proposed molecules (e.g., peptides) made from building block molecules (e.g., amino acids) in which an encoder matrix T is included in the neural network in accordance with some embodiments.

As shown in FIG. 1B, after process 200 begins at 102, the process receives the identities of building block molecules and functional properties of to-be-proposed molecules to be made from the building block molecules at 204.

Next, 106 and 108 of FIG. 1B are performed as described above in connection with 106 and 108 of FIG. 1A.

Then at 210, process 100 linearizes matrix $B_{known}$ to form vector $D_{known}$ in manner similar to that in which 114 of FIG. 1A linearizes matrix $C_{known}$ to for vector $D_{known}$ as described above.

At 116, process 200 then determines values $P_{known}$ for each vector $D_{known}$ as described above in connection with 116 of FIG. 1A.

Next at 217, process 200 initializes encoder matrix T with any suitable values. For example, in some embodiments, encoder matrix T is filled with values that correspond to the features in the one-hot codes in vector $D_{known}$ (like matrix T described in connection with FIG. 1A). As another example, in some embodiments, encoder matrix T is filled with random numbers. As yet another example, in some embodiments, encoder matrix T is filled with fixed numbers (e.g., all zeros, ones, etc.).

Finally, process 200 can perform 118 through 130 of FIG. 1B in the same manner as described above for 118 through 130 of FIG. 1A.

Figure 4:
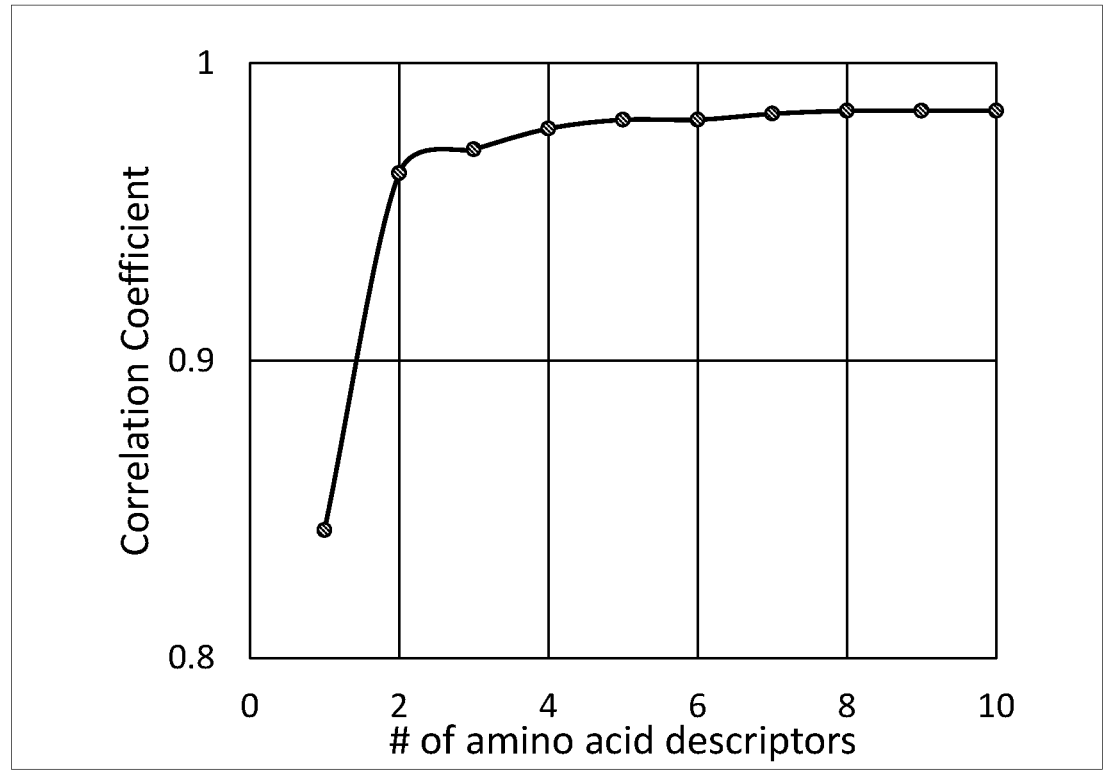
FIG. 4 is an example of the dependency of the accuracy of such a neural network on the number of descriptors that are used to describe each building block molecule (e.g., amino acid) in an encoder matrix T in accordance with some embodiments.

FIG. 4 illustrates an example of the dependency of the accuracy of such a neural network on the number of descriptors that are used to describe each building block molecule (e.g., amino acid) in an encoder matrix T in accordance with some embodiments. In this example, the encoder matrix T is not comprised of values for known building block molecule chemical properties (like matrix T of FIG. 1), but instead is initially filled with random numbers and the values in the encoder matrix T are then modified by the neural network. Surprisingly, in the example shown, even very simple descriptions using only two descriptors give >0.95 correlation and the correlation does not appreciably improve even with the addition of seven descriptors. The encoder matrix T acts as an information bottleneck, forcing the neural network to learn a compressed representation of the building block molecules (e.g., amino acids). In some embodiments of an implementation as described in FIG. 1A, the features (e.g. chemical properties such as charge, polarity, and size) describing the building block molecules (e.g., amino acids) need to be carefully selected to contain as much information important for predicting functional properties (e.g., peptide binding) as possible. When implemented as shown in FIG. 1B, the neural network is tasked with discovering a chemical space representation of the building block molecules (e.g., amino acids) optimized for modeling the relationship between the building block molecules and the functional properties of the proposed molecules (e.g., molecular interactions at the peptide-target interface).

Figure 5:
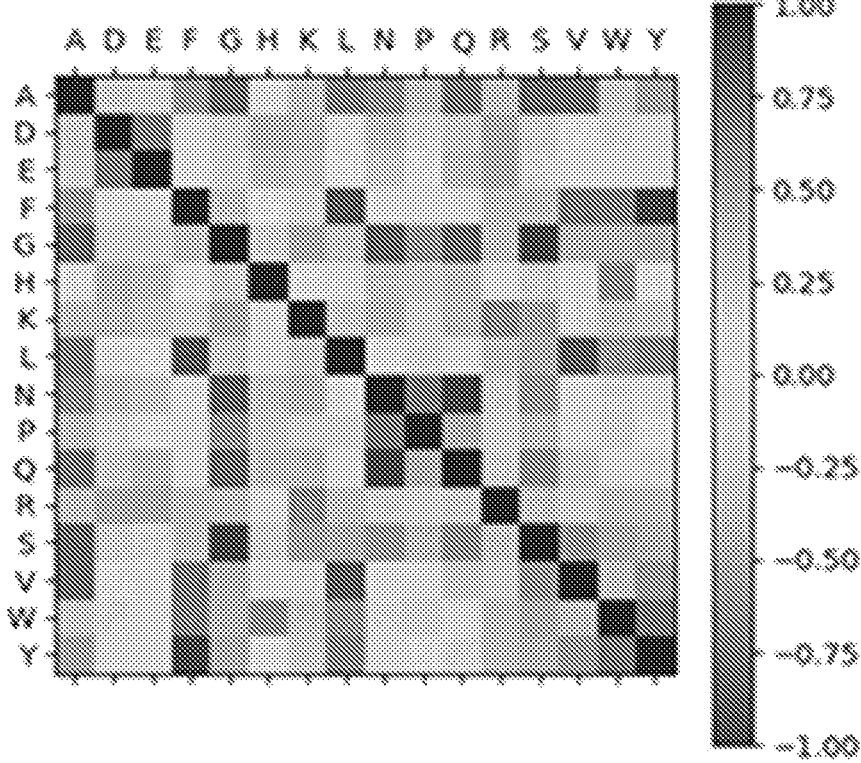
FIG. 5 is an example of a similarity matrix showing the chemistry learned by a neural network after training in accordance with some embodiments.

The chemistry learned by a neural network after training can be visualized with a similarity matrix (an example of which is shown in FIG. 5 for diaphorase; it is very similar for other proteins including Ferredoxin, Ferredoxin NADP reductase, PD1 receptor, PDL1, TNF alpha, TNF alpha receptor, Transferrin). For example, using the neural network trained in connection with FIG. 4, a similarity matrix can be calculated by first normalizing each row of the encoder matrix T to unit vector length, and then multiplying the encoder matrix T with its transpose. This results in a square matrix correlating the learned chemical space representations of the amino acids with each other (essentially the cosine between the vectors representing each amino acid). Comparison of the similarity matrices generated for diaphorase, ferredoxin, and ferredoxin NADPH reductase, for example, reveals a remarkable consistency in the chemistry learned by the neural network.

Figure 6:
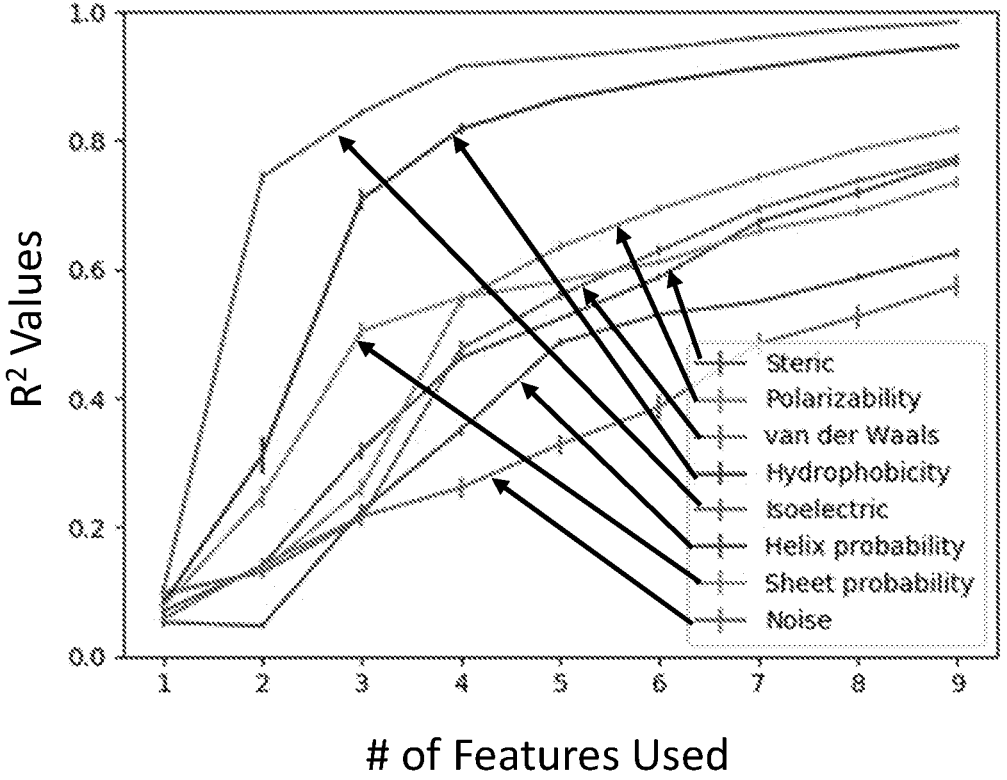
FIG. 6 is an example of the relative importance of the chemical properties in modeling binding at the peptide-target interface in accordance with some embodiments.

A more quantitative understanding of the chemistry learned by the neural network can be obtained by using the values in the encoder matrix T to describe the physical chemical properties of the building block molecules (to determine which physical/chemical properties of the building block molecules can be well described by combinations of the encoder matrix values). In this treatment, the quality of fit of the projection ($R^2$ coefficient between the predicted and measured values of functional properties of synthesized molecules) is used as a metric of how important the neural network decided each physical chemistry property was to model the functional properties (e.g., peptide binding) of the synthesized molecules. A plot of the projection $R^2$ values as a function of the number of features used for seven different chemical properties is shown in FIG. 6. $R^2$ values are the average of 100 different projections from independently trained encoder matrices T. A plot of the projection $R^2$ values as a function of the number of features used for random noise is also provided as the baseline $R^2$ coefficient that can be obtained by chance.

The example curves in FIG. 6 reveal the relative importance of the chemical properties in modeling binding at the peptide-target interface in accordance with some embodiments. Out of the seven chemical properties considered here, isoelectric point (strongly correlated with amino acid charge) is determined by the neural network as the most important parameter to learn for successfully modeling peptide binding. Isoelectric point is learned even when the neural network uses only two features. The second most important chemical concept learned is the interaction with water (hydrophobicity), which the neural network incorporates into its model once the neural network is using three or more features. Finally, second-order structural properties unique to side-chain geometry (sterics, van der Waals, and polarizability) are incorporated later when the neural network uses at least four features.

Figure 7:
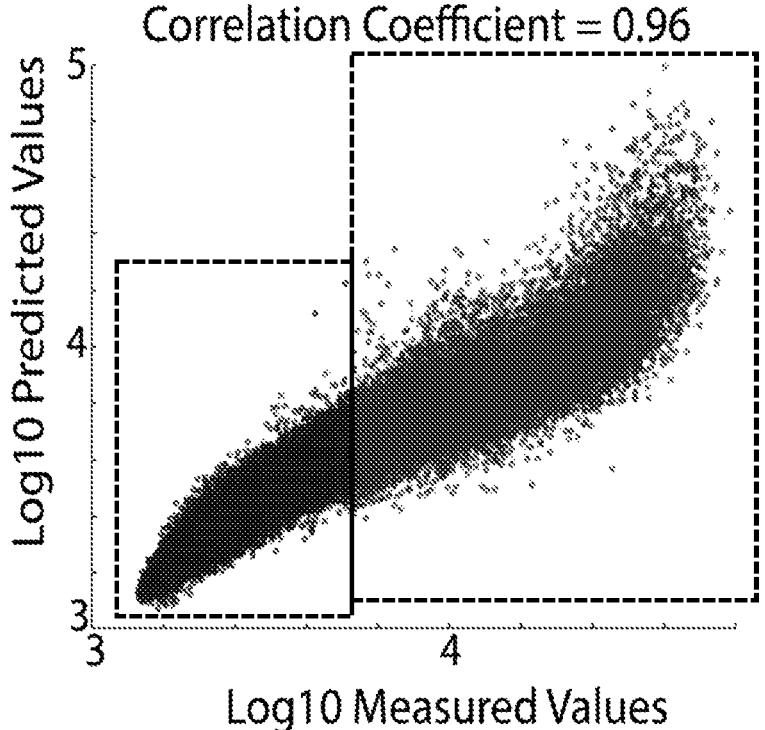
FIG. 7 is an example of graph showing that a trained neural network can predict peptide binding values more than an order of magnitude larger than the strongest binder of a training set in accordance with some embodiments.

In an experiment, a neural network was trained on a subset of a peptide array corresponding to weak binders and evaluated on its ability to predict binding values significantly larger than any it had seen before. As shown in FIG. 7, a trained neural network can predict peptide binding values in right dashed box more than an order of magnitude larger than the strongest binder of the training set in left dashed box, with a correlation coefficient of 0.96. The top binders are predicted especially well, an important feature for peptide drug discovery efforts.

Figure 8:
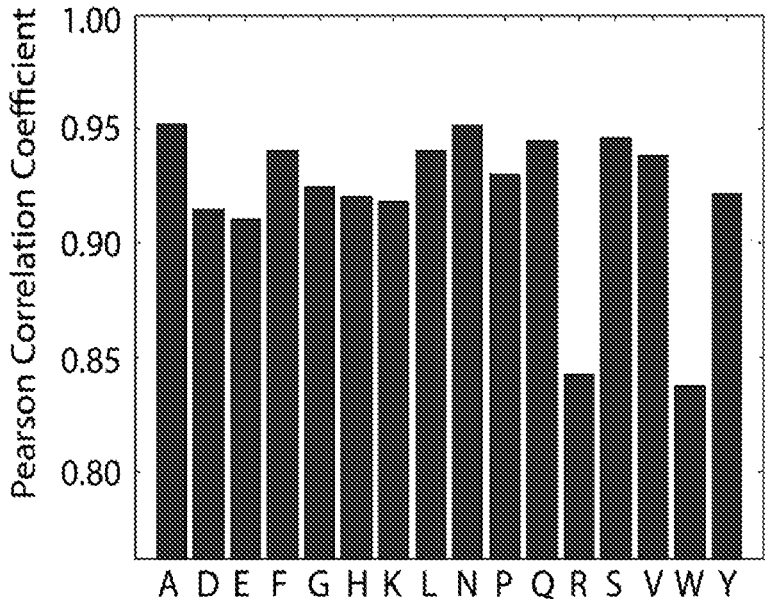
FIG. 8 is an example of the extrapolative performance for each of the building block molecules (in this case, amino acids) in accordance with some embodiments.

An example of the extrapolative performance for each of the building block molecules (in this case, amino acids) is shown in FIG. 8. Here, the encoder, T, was fixed and contained literature values of the physical properties of each of the amino acids used. Neural network training was performed on a subset of the known molecules (in this case, peptides) lacking a specific one of the building block molecules (in this case, amino acids) in their sequence, and the model was evaluated on the remaining known molecules (in this case, peptides) containing that building block molecule (in this case, the specific amino acid). Despite having never been trained to predict the function properties (in this case, the binding properties) of the left-out building block molecule (in this case, the specific amino acid), in most cases the extrapolation exceeds a correlation coefficient of 0.9. Only the building block molecules arginine (letter R in the x-axis) and tryptophan (letter W in the x-axis) exhibit correlation coefficients below 0.9, reflecting how chemically distinct they are compared with the other building block molecule amino acids. None of the other building block molecule amino acids contain anything similar to the guanidinium and indole groups that make arginine and tryptophan special, preventing the neural network from learning the chemistry it needs to extrapolate their binding properties. Better coverage of chemical space by including the remaining amino acids (cysteine, isoleucine, methionine, and threonine) as well as unnatural amino acids onto the arrays can be used to improve the ability to predict binding for new amino acids.

Figure 9:
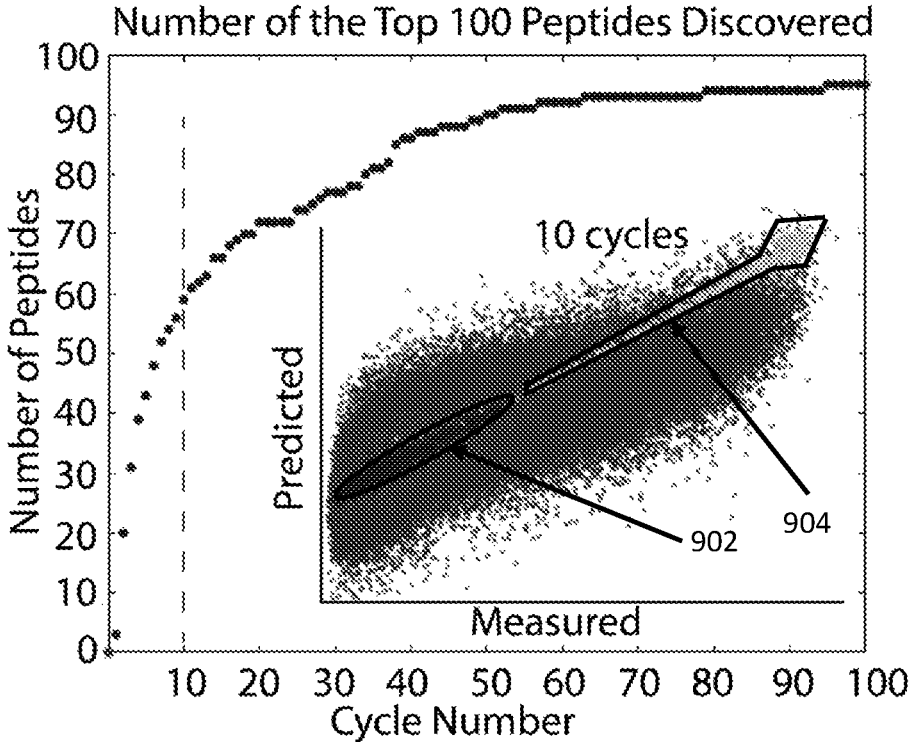
FIG. 9 is an example of a strategy for discovering molecules with the best function properties (e.g., strongest binding peptides) in accordance with some embodiments.

In some embodiments, as described above in connection with FIGS. 1A and 1B, iterative exploration of the structure/function space can be performed repeatedly training the neural network with an increasing library of synthesized molecules. This improves the model in the neural network each iteration and thus improves the prediction of which proposed molecules should be made next from which building block molecules (e.g., amino acids). An implementation of this strategy for discovering molecules with the best function properties (e.g., strongest binding peptides) is shown in FIG. 9 in accordance with some embodiments. The process started by randomly selecting 1000 known molecules (e.g., peptides) with low functional property values (e.g., binding values) (902 in FIG. 9) from an array and using these known molecules (e.g., peptides) to train a neural network. The neural network is then used to iteratively predict the molecules with the top 100 functional property values (e.g., tightest binding peptides) from the array that have not yet been used to train the neural network (904 in FIG. 9). These predicted molecules are then added to the neural network's training set, and then the neural network is retrained using the new training set. After only 10 cycles of this approach, 60% of the top performing (e.g., binding) molecules in the 125,000 molecule array were predicted. Using random sampling to find the top 60% high performing (e.g., binding) molecules would have taken >100 cycles. Thus, the efficiency/speed of searching this chemical space is increased more than 10-fold by taking advantage of the molecular recognition topology.

Figure 10:
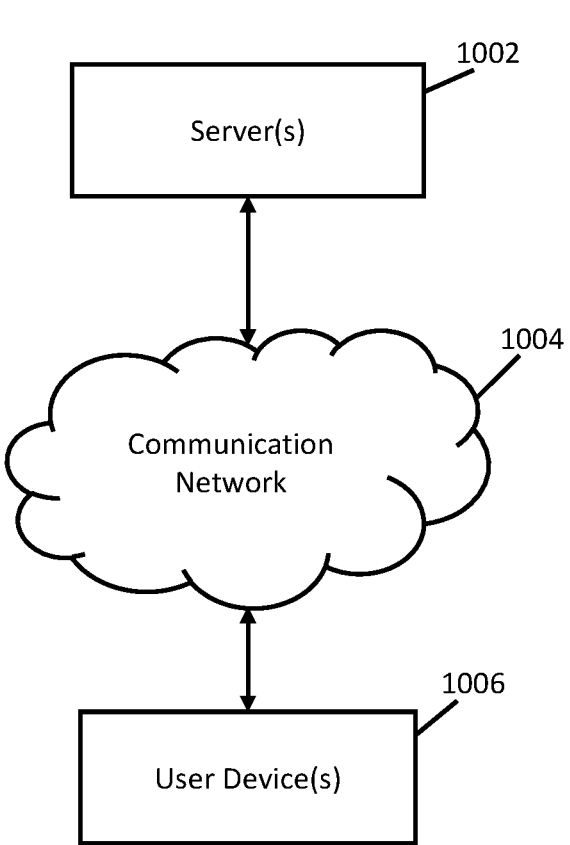
FIG. 10 is an example of hardware that can be used in accordance with some embodiments.

Turning to FIG. 10, an example 1000 hardware that can be used in accordance with some embodiments of the disclosed subject matter is shown. As illustrated, hardware 1000 can include one or more server(s) 1002, a communication network 1004, and a user device 1006.

Server(s) 1002 can be any suitable server(s) for predicting functions of molecular sequences. For example, in some embodiments, server(s) 1002 can store any suitable information used to train a neural network to predict functions of molecular sequences. As a more particular example, in some embodiments, server(s) 1002 can store sequence information (e.g., amino acid sequences of peptides, and/or any other suitable sequence information). As another more particular example, in some embodiments, server(s) 1002 can store data and/or programs used to implement a neural network. In some embodiments, server(s) 1002 can implement any of the techniques described above in connection with FIGS. 1-9. In some embodiments, server(s) 1002 can be omitted.

Communication network 1004 can be any suitable combination of one or more wired and/or wireless networks in some embodiments. For example, communication network 1004 can include any one or more of the Internet, a mobile data network, a satellite network, a local area network, a wide area network, a telephone network, a cable television network, a WiFi network, a WiMax network, and/or any other suitable communication network.

In some embodiments, user device 1006 can include one or more computing devices suitable for predicting functions of molecular sequences, and/or performing any other suitable functions. For example, in some embodiments, user device 1006 can store any suitable data or information for implementing and/or using a neural network to predict functions of molecular sequences. As a more particular example, in some embodiments, user device 1006 can store and/or use sequence information (e.g., sequences of amino acids in peptides, and/or any other suitable information), data and/or programs for implementing a neural network, and/or any other suitable information. In some embodiments, user device 1006 can implement any of the techniques described above in connection with FIGS. 1-9. In some embodiments, user device 1006 can be implemented as a laptop computer, a desktop computer, a tablet computer, and/or any other suitable type of user device.

Although only one each of server(s) 1002 and user device 1006 are shown in FIG. 10 to avoid over-complicating the figure, any suitable one or more of each device can be used in some embodiments.

Figure 11:
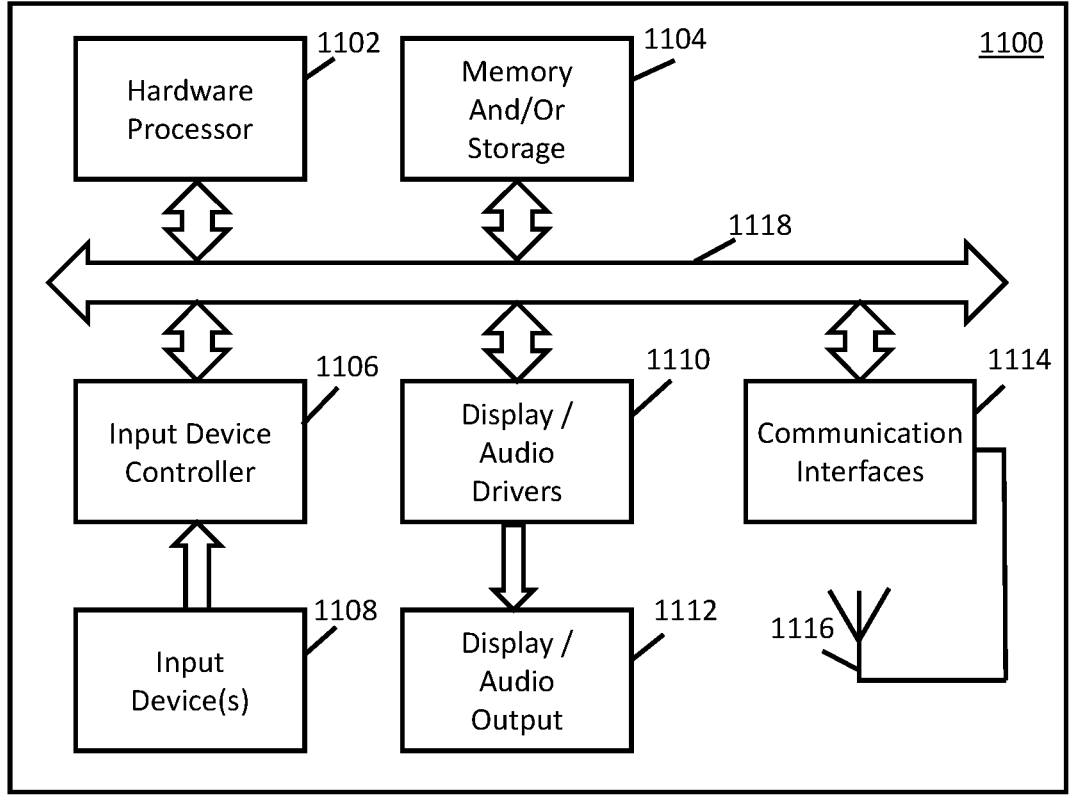
FIG. 11 is an example of more particular hardware that can be used in accordance with some embodiments.

Server(s) 1002 and/or user device 1006 can be implemented using any suitable hardware in some embodiments. For example, in some embodiments, devices 1002 and 1006 can be implemented using any suitable general-purpose computer or special purpose computer. For example, a server may be implemented using a special purpose computer. Any such general-purpose computer or special purpose computer can include any suitable hardware. For example, as illustrated in example hardware 1100 of FIG. 11, such hardware can include hardware processor 1102, memory and/or storage 1104, an input device controller 1106, an input device 1108, display/audio drivers 1110, display and audio output circuitry 1112, communication interface(s) 1114, an antenna 1116, and a bus 1118.

Hardware processor 1102 can include any suitable hardware processor, such as a microprocessor, a micro-controller, digital signal processor(s), dedicated logic, and/or any other suitable circuitry for controlling the functioning of a general purpose computer or a special purpose computer in some embodiments.

Memory and/or storage 1104 can be any suitable memory and/or storage for storing programs, data, and/or any other suitable information in some embodiments. For example, memory and/or storage 1104 can include random access memory, read-only memory, flash memory, hard disk storage, optical media, and/or any other suitable memory.

Input device controller 1106 can be any suitable circuitry for controlling and receiving input from a device in some embodiments. For example, input device controller 1106 can be circuitry for receiving input from a touch screen, from one or more buttons, from a voice recognition circuit, from a microphone, from a camera, from an optical sensor, from an accelerometer, from a temperature sensor, from a near field sensor, and/or any other type of input device.

Display/audio drivers 1110 can be any suitable circuitry for controlling and driving output to one or more display/audio output circuitries 1112 in some embodiments. For example, display/audio drivers 1110 can be circuitry for driving an LCD display, a speaker, an LED, or any other type of output device.

Communication interface(s) 1114 can be any suitable circuitry for interfacing with one or more communication networks, such as network 1004 as shown in FIG. 10. For example, interface(s) 1114 can include network interface card circuitry, wireless communication circuitry, and/or any other suitable type of communication network circuitry.

Antenna 1116 can be any suitable one or more antennas for wirelessly communicating with a communication network in some embodiments. In some embodiments, antenna 1116 can be omitted when not needed.

Bus 1118 can be any suitable mechanism for communicating between two or more components 1102, 1104, 1106, 1110, and 1114 in some embodiments.

Any other suitable components can be included in hardware 1100 in accordance with some embodiments.

It should be understood that at least some of the above described blocks of the process of FIG. 1 can be executed or performed in any order or sequence not limited to the order and sequence shown in and described in the figures. Also, some of the above blocks of the process of FIG. 1 can be executed or performed substantially simultaneously where appropriate or in parallel to reduce latency and processing times. Additionally or alternatively, some of the above described blocks of the process of FIG. 1 can be omitted.

In some embodiments, any suitable computer readable media can be used for storing instructions for performing the functions and/or processes herein. For example, in some embodiments, computer readable media can be transitory or non-transitory. For example, non-transitory computer readable media can include media such as non-transitory magnetic media (such as hard disks, floppy disks, and/or any other suitable magnetic media), non-transitory optical media (such as compact discs, digital video discs, Blu-ray discs, and/or any other suitable optical media), non-transitory semiconductor media (such as flash memory, electrically programmable read-only memory (EPROM), electrically erasable programmable read-only memory (EEPROM), and/or any other suitable semiconductor media), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

In connection with FIGS. 12-38, below are descriptions of experiments performed to evaluate some embodiments described herein.

Nine different proteins were fluorescently labeled and incubated with one of three different peptide array formats, washed and scanned (proteins are listed in FIG. 12, details in Tables S1 and S2 below, and FIG. 26 and associated text). The array consisted of either ~126,000 or ~123,000 unique peptide sequences, synthesized directly on a silica coated silicon wafer and cut into microscope slide sized pieces, each slide with 24 arrays. For each protein, data from 2-3 replicates was averaged. The values used in the neural network-based fits were $\log_{10}(counts+100)$, where "counts" are the unnormalized fluorescent counts recorded by an array scanner. The addition of 100 to each fluorescent count both avoided taking the logarithm of zero and suppressed large fluctuations due to noise. Typically, the noise level in these binding assays is a few hundred counts and the dynamic range is typically 100-300 fold above the noise. Note that all correlations reported are between data on log scales.

A shallow feedforward neural network was used to model the binding interactions between the peptides on the array and their target. Each peptide sequence was represented as a fixed-size binary matrix (sequence position×amino acid). Each row is a vector of zeros and a one to indicate the amino acid at that position in the sequence. Unused rows for shorter peptides were filled with zeros. This matrix was passed through an encoder that linearly transforms each binary amino acid into a dense continuous representation. The encoded matrix was then flattened to form a real-valued vector representation of the sequence. A neural network with two hidden layers (100 nodes each with the rectified linear unit activation function applied to the output) was then used to predict the target binding value for each peptide sequence (see FIGS. 23-25 and associated text in the Supplementary Information for more details). This machine learning approach is computationally rapid and, as described below, lends itself to chemical interpretation. Note that most of the calculations were performed on stand-alone workstations with 18-20 cores. When a parallel batch approach is used on one of these machines, >50 independent fits per hour can be executed.

Figure 13:
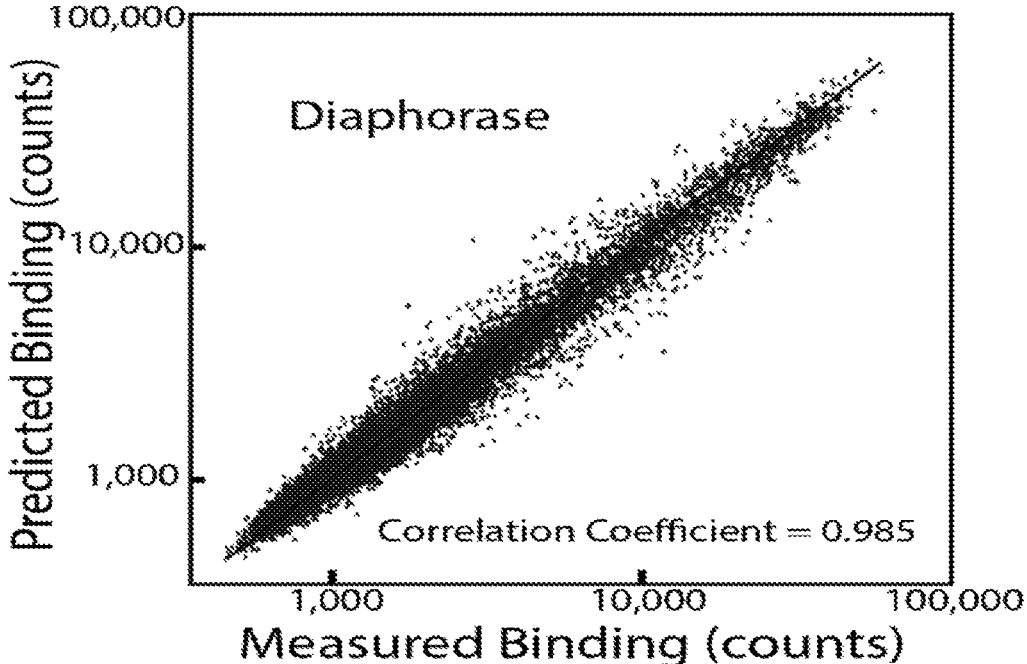
FIG. 13 is an example of predicted versus measured binding values using the fluorescently labeled enzyme, diaphorase, as the target in accordance with some embodiments.
Figure 27:
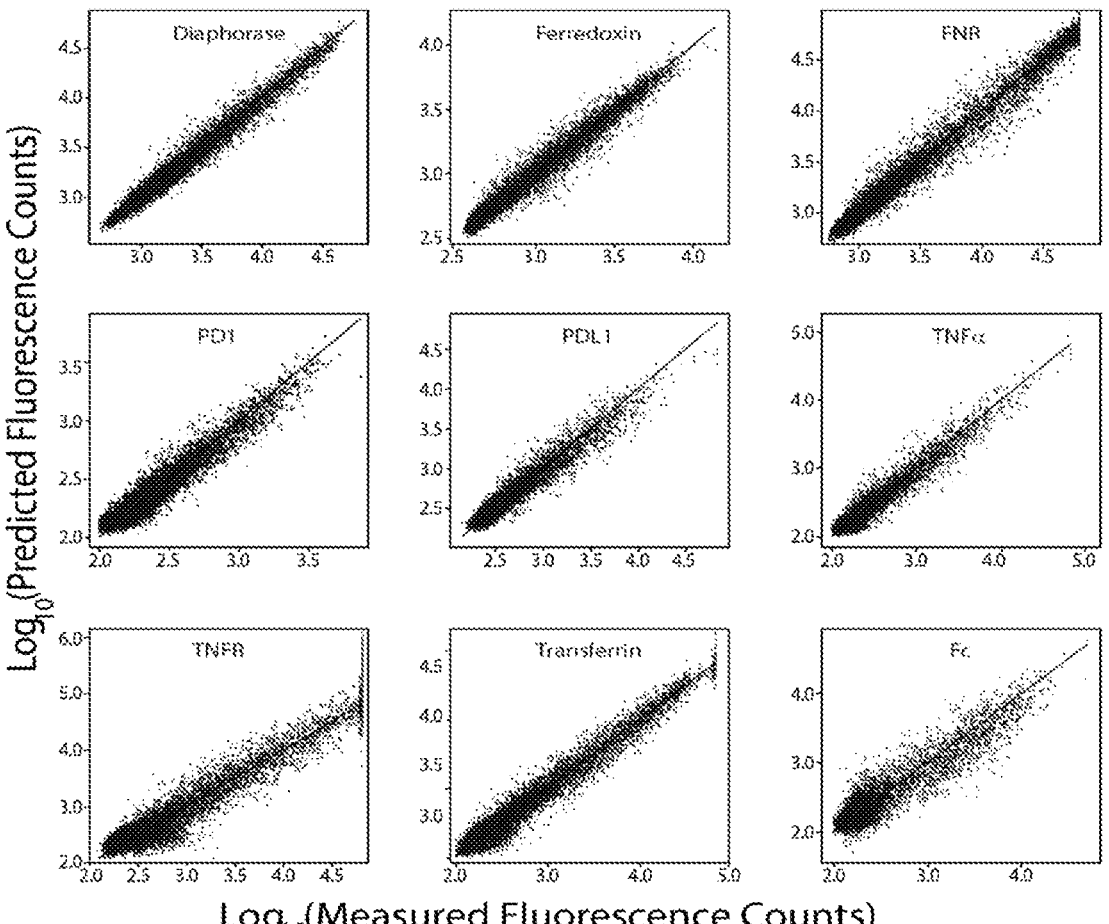
FIG. 27 is an example of predicted vs. measured binding values on a logarithmic scale for nine proteins for which experiments were performed in accordance with some embodiments.

FIG. 13 shows an example of the predicted versus measured binding values using the fluorescently labeled enzyme, diaphorase, as the target in accordance with some embodiments. The binding values measured for 90% of the peptide sequences on the array (~113,000 peptides) were used to train the model, with the remaining 10% of sequences (validation set of ~13,000 peptides) used to cross-validate the model's performance. The Pearson correlation coefficient between the $\log_{10}$ of the predicted and measured values in the validation set was $0.985\pm0.001$ for 100 runs with randomly selected training and test sets, nearly the same as the correlation between multiple array binding measurements (~0.99, Table S2 below). The fit is thus limited by the signal-to-noise of the experimental measurement. Similar results have been obtained for the nine purified proteins shown in FIG. 12 (FIG. 27). The training and test sets are chosen nearly randomly from all possible peptide sequences, implying that sampling only ~$10^5$ sequences is sufficient to accurately describe the target binding over the entire space of $10^{12}$ sequences. (The photolithographic method of array synthesis does bias the sequence representation on the array away from purely random slightly, but it should not affect the results presented here).

Figure 14:
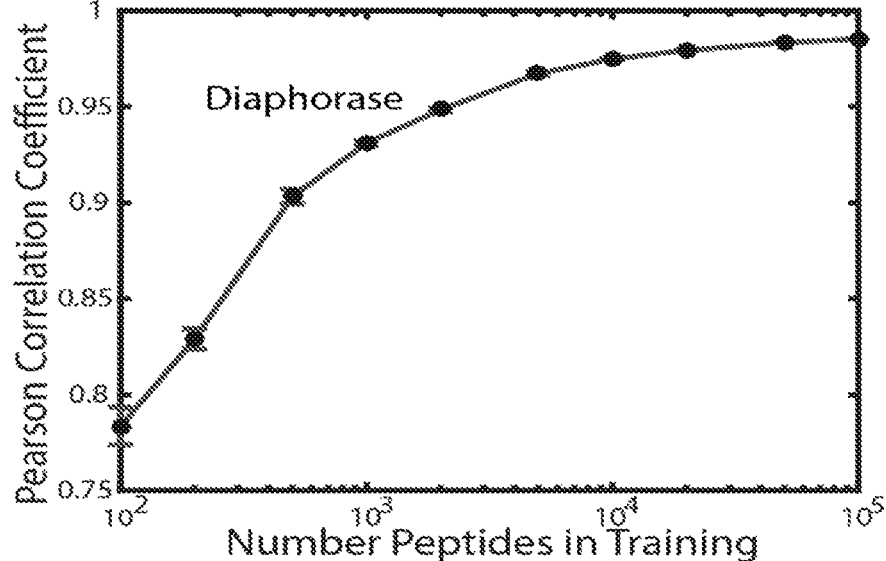
FIG. 14 is an example of a graph showing predicted binding vs. measuring binding of molecules in accordance with some embodiments.
Figure 28:
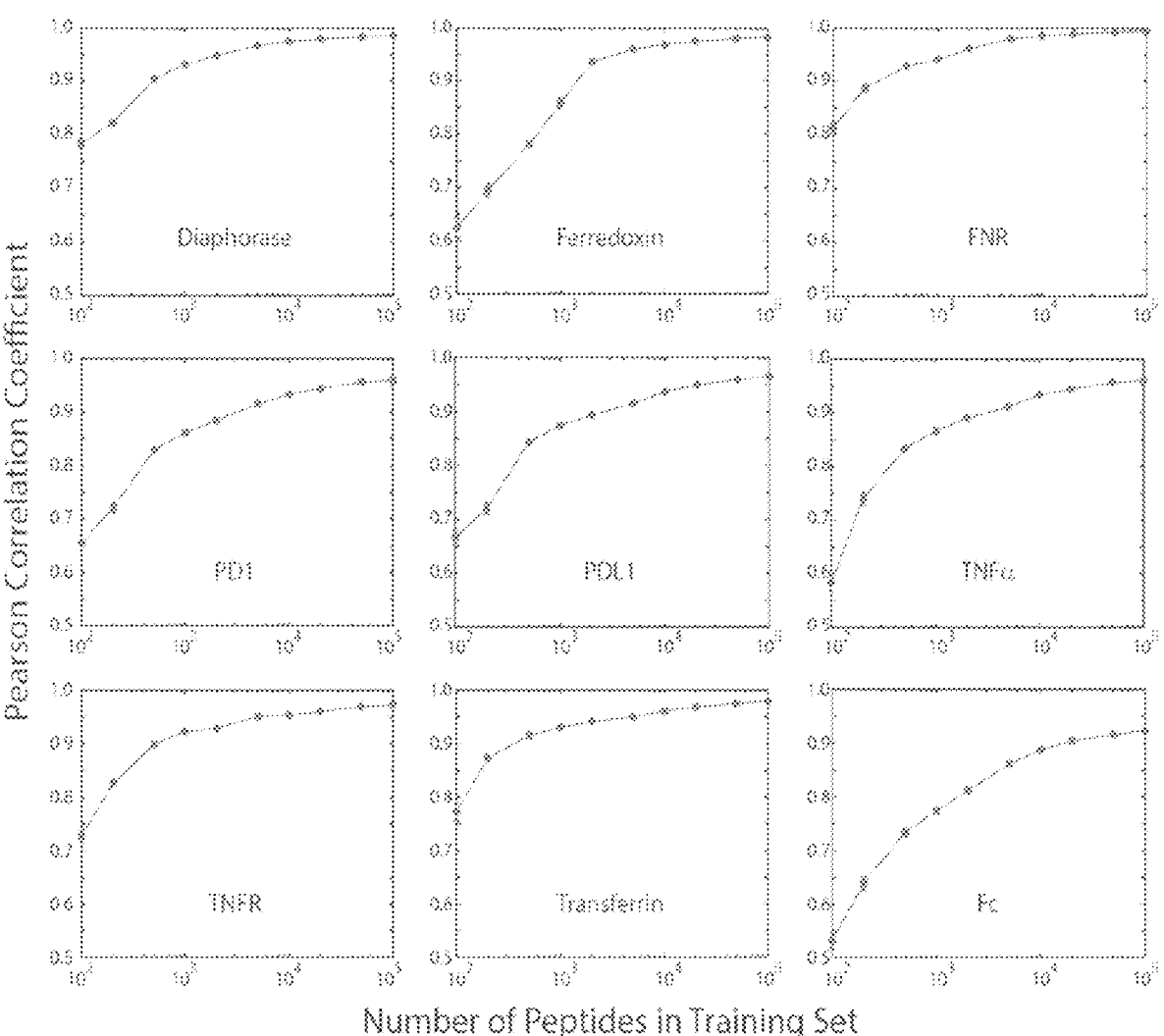
FIG. 28 is an example of correlation coefficients between the predicted and measured binding values plotted as a function of the training set size in accordance with some embodiments.

The model performance was determined as a function of training set size between 100 and 100,000 peptides (shown for diaphorase in FIG. 14). Training with as few as ~1000 peptides gives a correlation coefficient of >0.9 between the predicted and measured values. Similar results were obtained for most of the other proteins tested (FIG. 28). The correlation coefficient appears to be near its maximum by 100,000 peptides in most cases; increasing the sampling by an order of magnitude is unlikely to result in a qualitative model improvement.

Figures 15A, 15B:
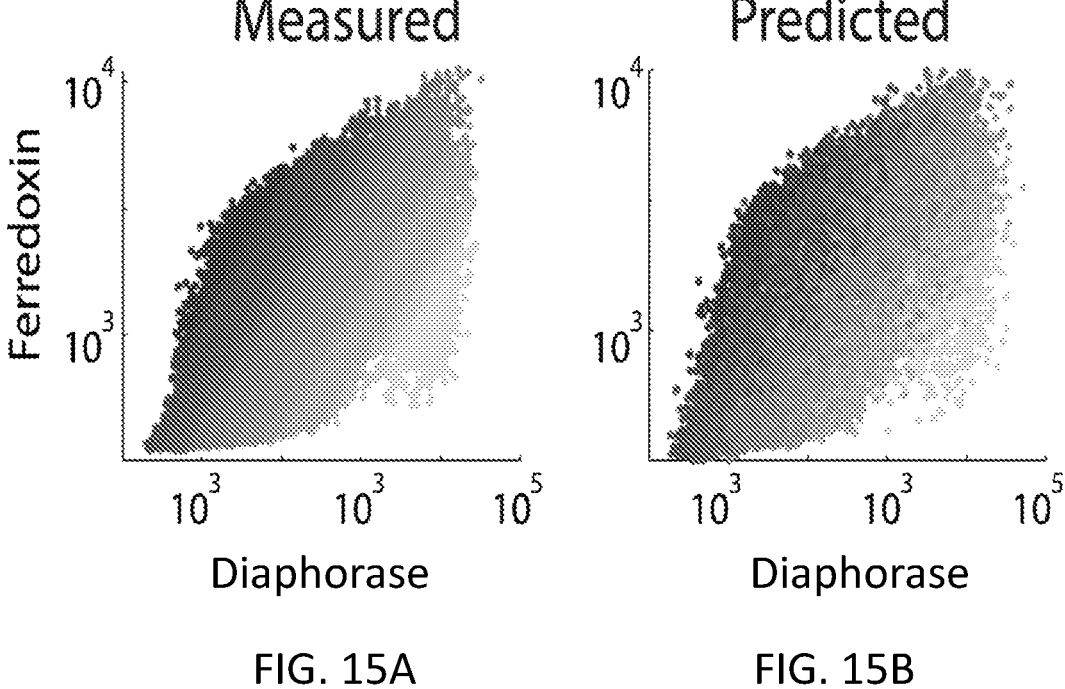
FIG. 15A is an example of a scatter plot comparing the measured binding values for diaphorase and ferredoxin for a set of 36,000 array peptides in accordance with some embodiments.
FIG. 15B is an example scatter plot that shows a comparison of the predicted binding values of the validation set for the two proteins referenced in FIG. 15A.

Diaphorase, ferredoxin, and FNR listed in FIG. 12 were measured using identical peptide arrays, under the same conditions, and at the same time. This provides an opportunity to ask how well the model predicts binding specific to a given target. A example scatter plot comparing the measured binding values for diaphorase and ferredoxin for a set of 36,000 array peptides is shown in FIG. 15A in accordance with some embodiments. Note that the distribution is very wide (this is a log scale), meaning that the values for a particular sequence can be quite different between the two proteins. Sequences that bind more strongly to ferredoxin than to diaphorase are dark colored, whereas lighter points indicate stronger binding to diaphorase. FIG. 15B illustratively compares the neural network predicted binding values for the same 36,000 peptides used in FIG. 15A, where the remaining peptides on the array were used to train the model. Importantly, both the shape and color distributions are very similar in the two panels. Thus, there is both significant target-specific binding on these arrays, and this specific binding is captured by the model. Analyses for the other protein pairs (diaphorase vs. Ferredoxin-NADP reductase (FNR) and FNR vs. ferredoxin), as well as all combinations of Programmed Cell Death protein 1 (PD1), Programmed Cell Death protein 1 Ligand (PDL1), Tumor Necrosis Factor alpha (TNF alpha), and Receptor for Tumor Necrosis Factor alpha (TNFR) (this set of proteins was also measured under identical conditions), are given in FIG. 29.

Figure 16:
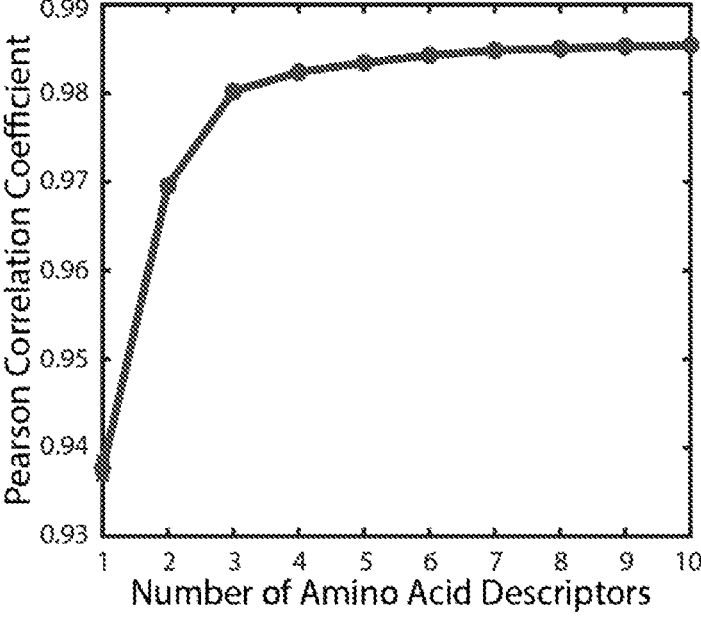
FIG. 16 is an example of a graph showing model performance as a function of the number of descriptors used in accordance with some embodiments.
Figure 30:
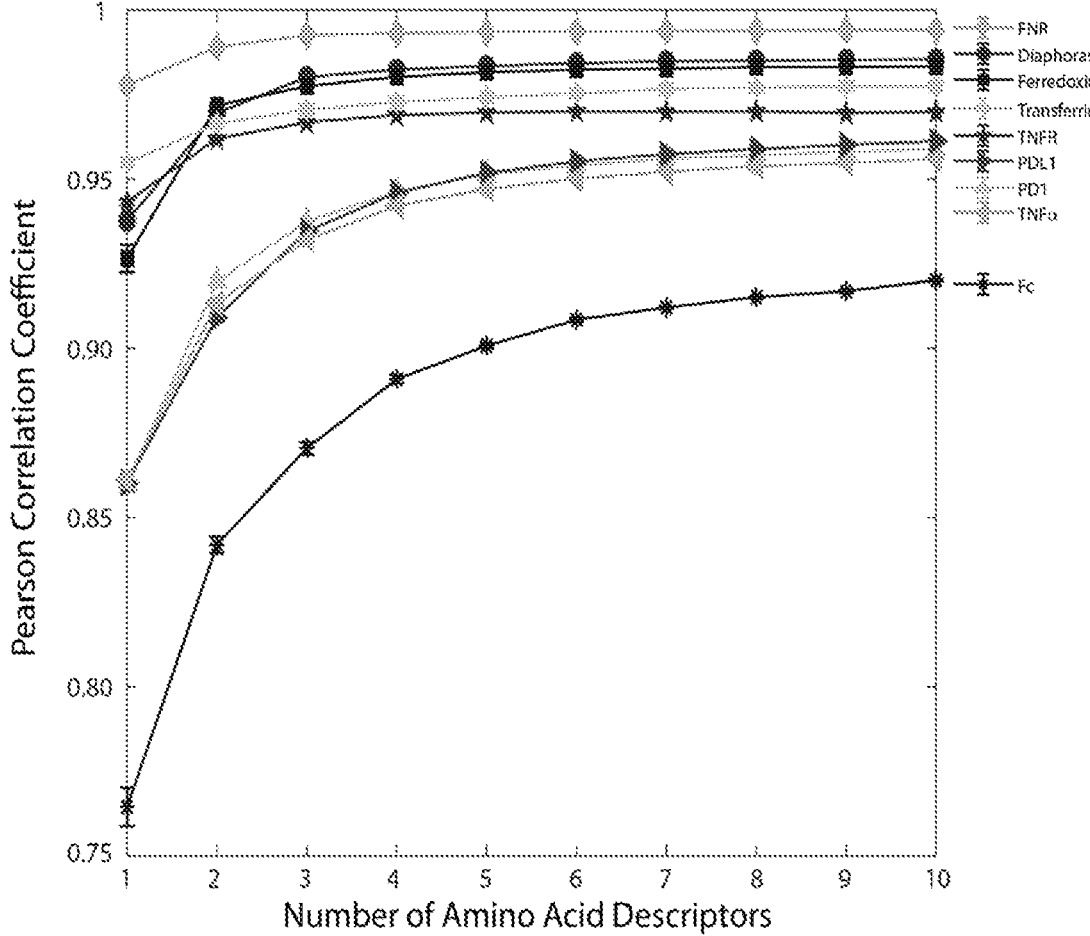
FIG. 30 is an example of correlation coefficients between the predicted and measured binding values vs. the number of amino acid descriptors used in the encoder matrix in accordance with some embodiments.

In the analysis above, each amino acid is assigned a vector representation (a set number of descriptors) that is optimized during the fitting process. This encoding acts as an information bottleneck, forcing the neural network to learn a compressed representation of the amino acids; the resulting descriptors presumably contain information about amino acid chemical properties that is necessary for modeling the binding of peptide sequences to that target (e.g. charge, polarity, size). Model performance as a function of the number of descriptors used is shown in FIG. 16 for diaphorase and demonstrates that only a very simple representation of each amino acid is required: using as few as 2 descriptors gives >0.95 correlation, and no appreciable improvement occurs with >7 descriptors. Similar results are seen for the other proteins (FIG. 30).

Figure 17:
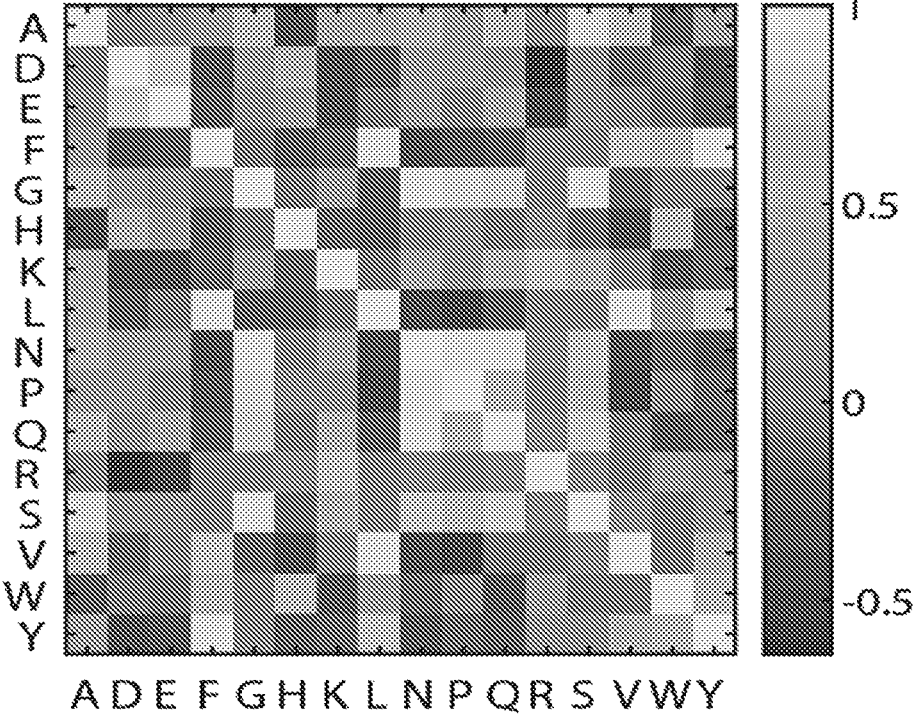
FIG. 17 is an example of a target-specific amino acid similarity matrix in accordance with some embodiments.
Figure 31:
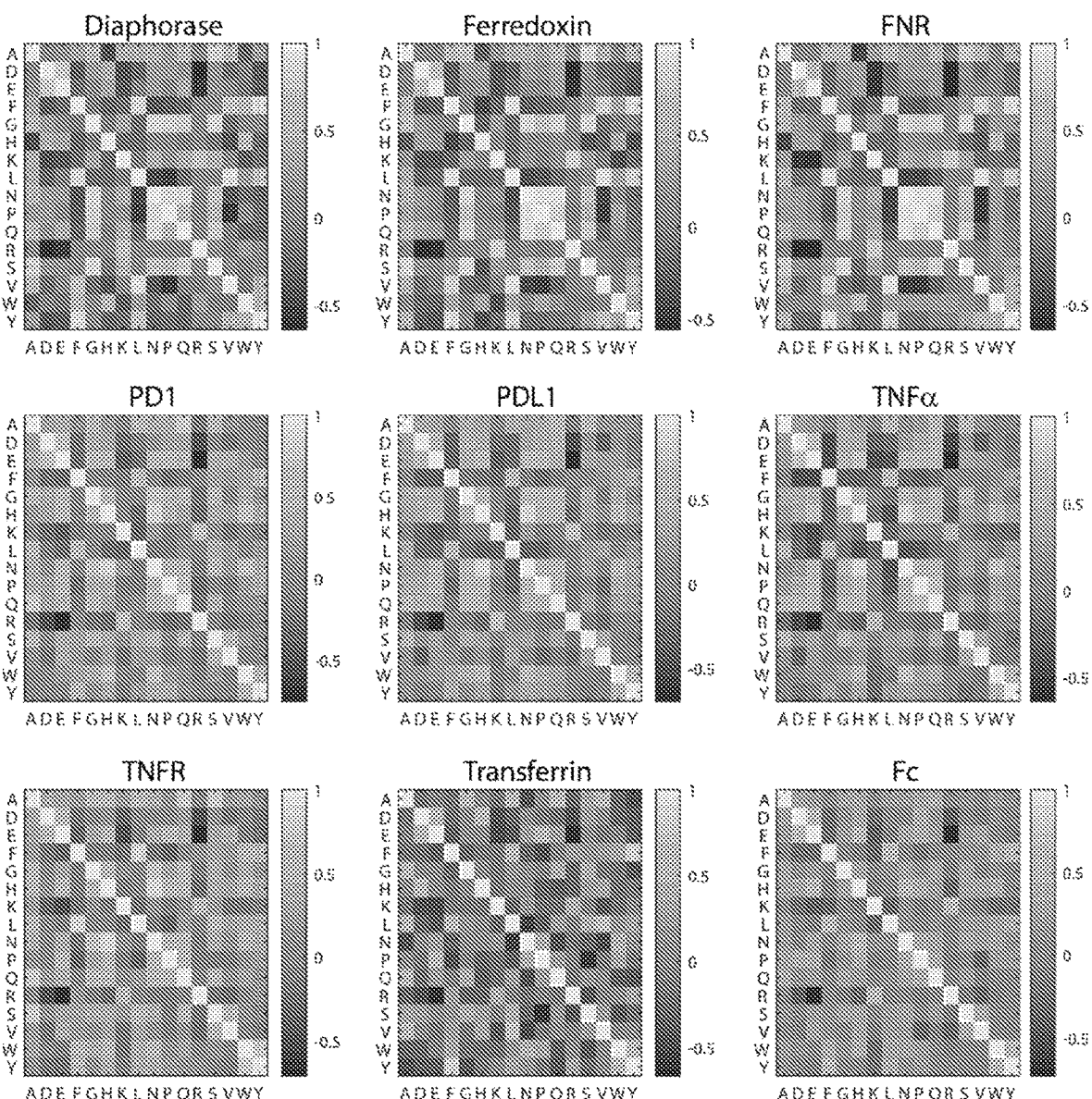
FIG. 31 is an example of heat maps of the similarities between amino acid feature vectors learned by the neural network in accordance with some embodiments.

One can create a target-specific amino acid similarity matrix by calculating the orthogonality of each possible amino acid pair using the learned vector representations of the amino acids (FIG. 17). Orthogonality is represented as the normalized dot product of the learned vector representations, and is given as a heat map. In this map, a value of 1 means that the vectors describing the amino acids being compared are parallel (are related by a positive proportionality constant, e.g. two very similar amino acids like asparagine and glutamine), 0 means they are orthogonal (there is no similarity in the context of the binding on the array such as glutamic acid and valine) and −1 means that they are parallel but opposite (are related by a negative proportionality constant, e.g., glutamic acid and lysine which both have charges but in opposite directions). The result generally agrees with chemical intuition, with structurally related amino acids being near parallel (D&E, N&Q, F&Y, L&V, G&S) and amino acids with a common but opposite characteristic (charge) having a negative relationship (D&E vs. K&R). Most proteins tested have comparable results, as the similarity matrices reflect an average of all the molecular interactions at the peptide-target interface. That said, there are significant differences in the target-specific similarity matrices of a few proteins (FIG. 31).

Figure 18:
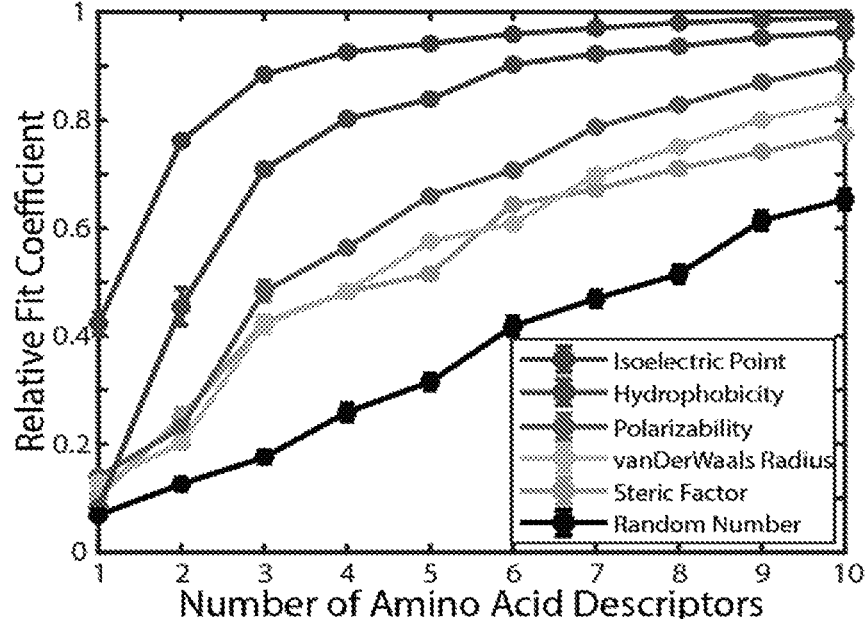
FIG. 18 is an example of a graph showing relative fit coefficient vs. number of amino acid descriptors in accordance with some embodiments.

The chemistry learned by the neural network can be quantified by projecting the learned amino acid feature vectors onto the space of known physical chemical properties. Example results are shown in FIG. 18 for diaphorase and in FIG. 32 for the other proteins in accordance with some embodiments. Here, five common chemical properties, as well as a set of random values as a negative control, were fit to a linear combination of the descriptors for all 16 amino acids simultaneously (amino acids properties taken from). The plot shows the quality of the fit, measured as the $R^2$ coefficient averaged over 100 fits, as a function of the number of descriptors. When only one descriptor is available to represent the amino acids, isoelectric point (charge) is the only chemical property out of those tested that is significant within the learned representation. Isoelectric point continues to be the most dominant contribution for larger numbers of descriptors, followed by hydrophobicity. There are smaller contributions from sterics (graph shape index), the van der Waals term (related to side chain volume), and polarizability. Based on this and the similarity matrix, it is evident that the descriptors that the network chooses for each amino acid contain information about known chemical properties of that amino acid.

Figure 19:
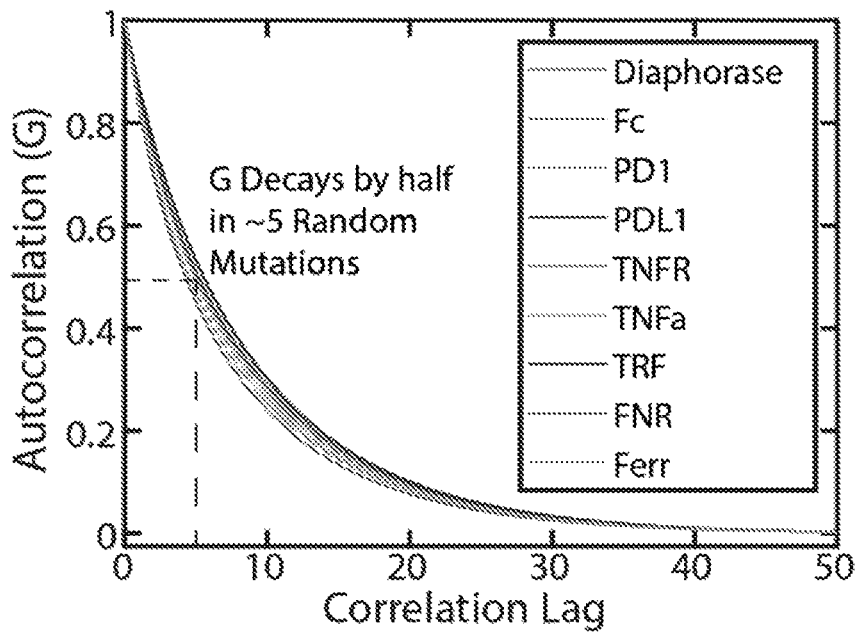
FIG. 19 is an example of a graph showing autocorrelation vs. correlation lag in accordance with some embodiments.

The results described above support the idea that the relationship between peptide sequence and binding is well behaved: most amino acid changes in a local region of sequence space result in modest changes in binding. In FIG. 19, an example of this concept is quantitatively evaluated in accordance with some embodiments. In this study, a specific peptide sequence is randomly selected and then a random walk (10,000 random mutations of the sequence) is performed, and at each point in the random walk the predicted $\log_{10}$(binding) is calculated using the neural network model for a particular target protein. This effectively reduces the topology of the space to one dimension. By then performing autocorrelation of the random walk binding trace, one can learn how many random mutations it takes on average to walk off of, or onto, a molecular recognition feature. For each protein, this was repeated 500,000 times using randomly selected starting sequences and averaged. As can be seen in FIG. 19, the result is remarkably consistent regardless of which protein is bound to the array, with 5 random mutations dropping the correlation function by about half for a peptide sequence 10 amino acids long, and 20-30 mutations taking the correlation to near zero, more or less irrespective of the protein used (for detailed values see FIG. 33). It is important to recognize that these are random mutations taking place at random positions in a peptide that is short enough to likely be unstructured. One is effectively measuring how many such mutations result in a peptide sequence "forgetting" its origin. Thinking about this from an evolutionary perspective, it suggests that an unstructured sequence of about 10 amino acids can vary by a Hamming distance of roughly 5 and maintain some of its original molecular recognition properties.

Figure 20:
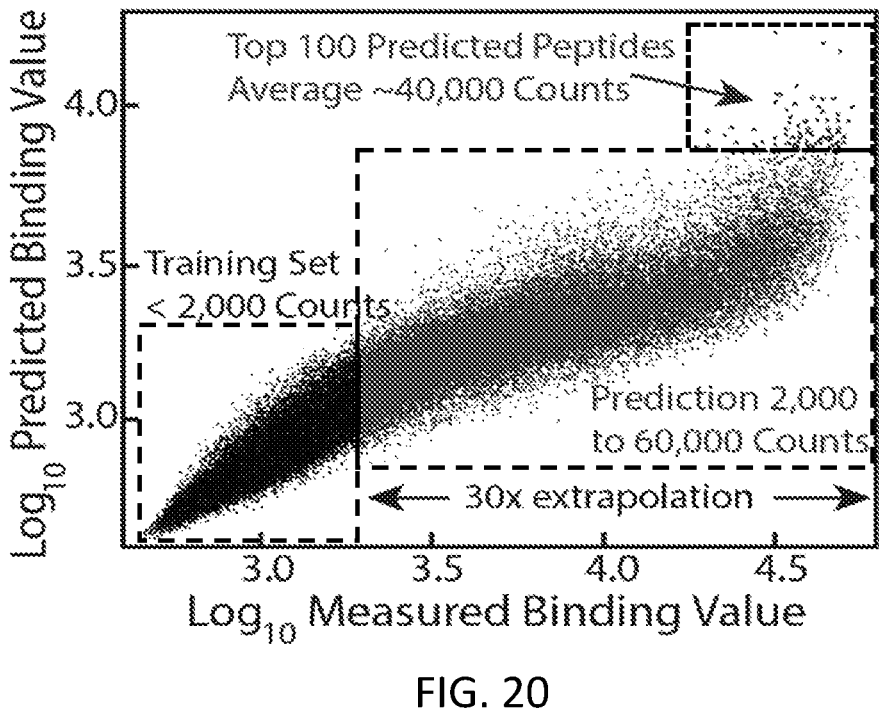
FIG. 20 is an example of a graph showing predicted binding value vs. measured binding value in accordance with some embodiments.

In the examples above, the neural network was used to interpolate the binding values within a library of peptide sequences. It would be even more useful if the algorithm extrapolated accurately outside of the binding values of the original training set. In FIG. 20, the neural network was trained on a subset of weak binding peptide sequences with binding values that are within a factor of 5 of the lowest binding value in accordance with some embodiments. For diaphorase, these are sequences with binding signals <2000 counts (FIG. 20, left dashed box points, see FIG. 34 for different ranges of training values). The resulting model is then evaluated on its ability to predict the binding signals of sequences with much stronger binding (FIG. 20, right dashed box points). For diaphorase, the trained model predicts peptide sequences with binding values up to 30-fold larger than the strongest binding signal of the training set, and the highest 100 predicted values have measured binding signals averaging ~40,000 counts (top dashed box). Similar results are found for the other 8 proteins (FIG. 35). Overall, the neural network is effective at extrapolating to sequences that show one to two orders of magnitude increase in binding.

Figure 21:
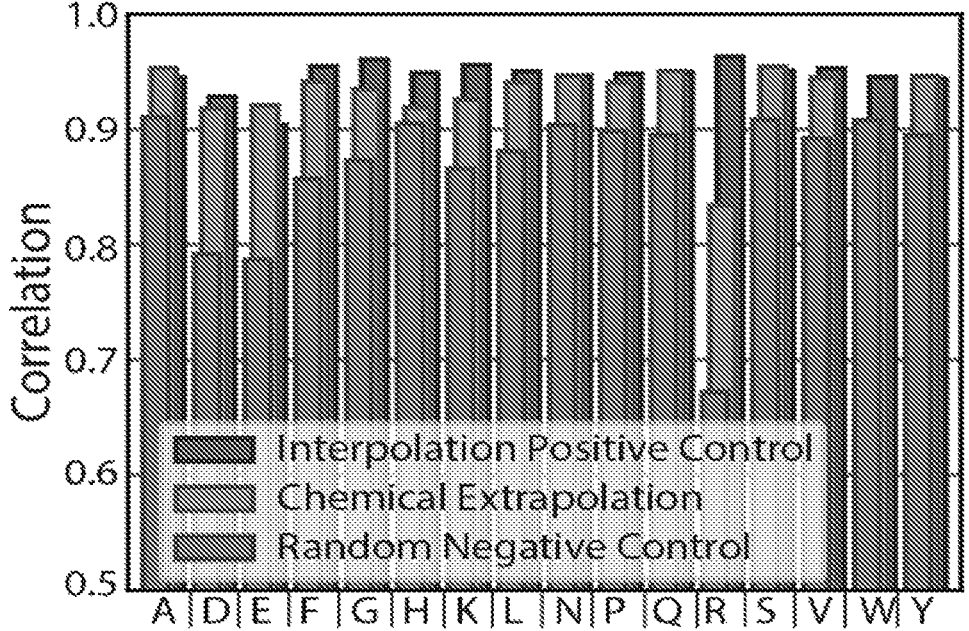
FIG. 21 is an example of a bar graph for amino acids vs correlation in accordance with some embodiments.

In addition to extrapolation in sequence space, it has also been possible to extrapolate to new chemistries. In all the work above, the amino acid descriptors were determined by the neural network. However, if instead the encoder matrix is replaced with measured chemical properties of the amino acids from the literature and not allowed to vary during training, the neural network is forced to learn how to use the chemical properties of the amino acids to predict binding. This is a particularly difficult problem because there are only 16 different amino acids used in the synthesis on the array and it would be very easy to overfit the data (i.e., the range of chemical examples to learn from is limited). Thus, we only used 3 chemical properties per amino acid: isoelectric point, hydrophobicity, and van der Waals radius. The extrapolation was attempted for only three proteins (diaphorase, FNR and ferredoxin) as these three proteins were assayed on commercial arrays (HealthTell, Inc.) that were synthesized and tested under highly optimized conditions, minimizing common amino acid modifications such as oxidation of histidine or tryptophan and providing the highest reproducibility between replicates (Table S2 below). In FIG. 21, the neural network was trained on the subset of peptides lacking one of the amino acids in their sequence, and the model was evaluated on the remaining peptides containing that amino acid and using the chemical properties of that amino acid as input in accordance with some embodiments. For example, the third bar set of FIG. 21 is the result for glutamic acid. A neural network was trained on the 57,782 sequences in the array that completely lack glutamic acid. This was done using the chemical properties of the other amino acids as the values in the encoder matrix, and then it was tested on its ability to predict binding for the 68,268 sequences that contain glutamic acid, using an encoder matrix that includes chemical properties for glutamic acid. Thus, it has the opportunity to learn about chemical properties from the other 15 amino acids and apply that learned information to the peptides containing glutamic acid and predict their binding values (the middle row is the correlation between predicted and observed for the glutamic acid containing peptides). As a negative control, random values were used for the properties of the amino acid left out of the training (the front row bar is an average of 100 random sets). For glutamic acid, the use of the chemical properties of glutamic acid gave rise to a much better prediction than simply using random values (middle row vs. front row). The positive control involved training and testing on the set of peptides that contain the particular amino acid in question (back row bar, 90% used for training). Despite having never been trained to predict the binding properties of glutamic acid, the extrapolation does as well as the positive control (the middle row is about the same height as the back row bar). For most amino acids the neural network prediction based on its learned chemistry from other amino acids is near the positive control. The cases where the neural network has the most trouble are easy to understand; histidine, lysine, arginine and tryptophan are all amino acids that have unique chemical properties that could not be learned by comparison to the other amino acids. Note however that for all amino acids except tryptophan, some chemistry is learned: the extrapolation using the real chemical properties (middle row) is higher on average than the random value extrapolations (front row, See FIG. 36 for FNR and ferredoxin).

Figure 22:
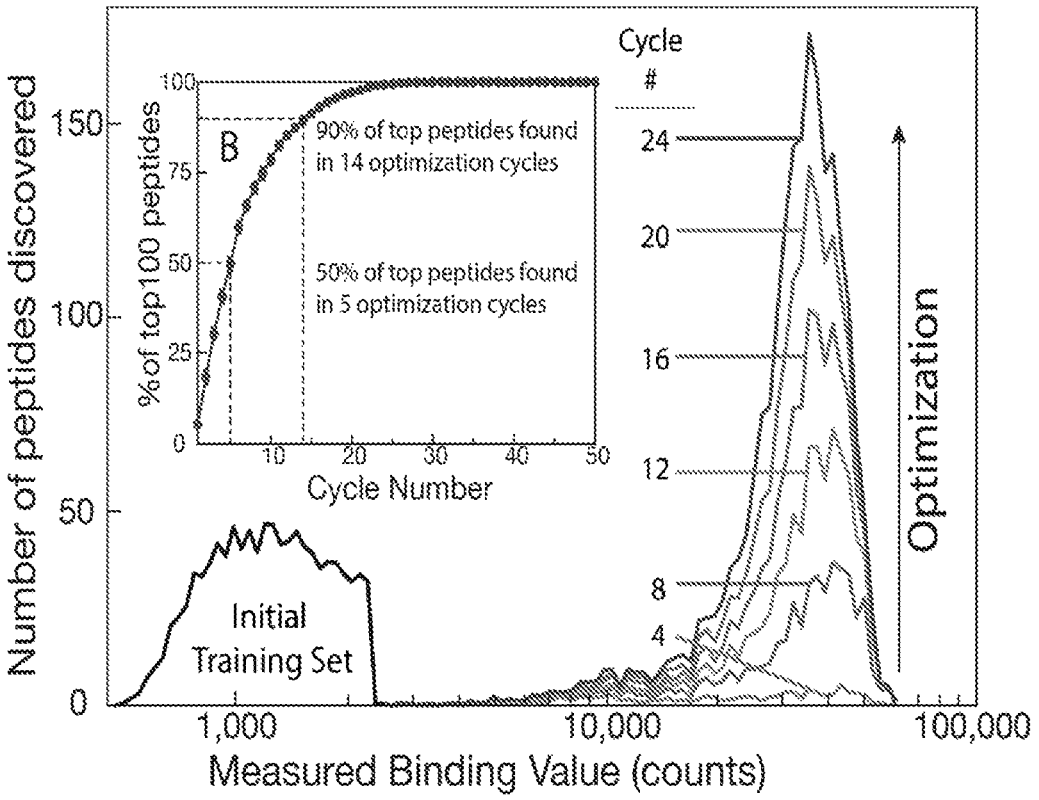
FIG. 22 is an example of distribution of binding strengths as a function of optimization cycle number for diaphorase in accordance with some embodiments.
Figure 37:
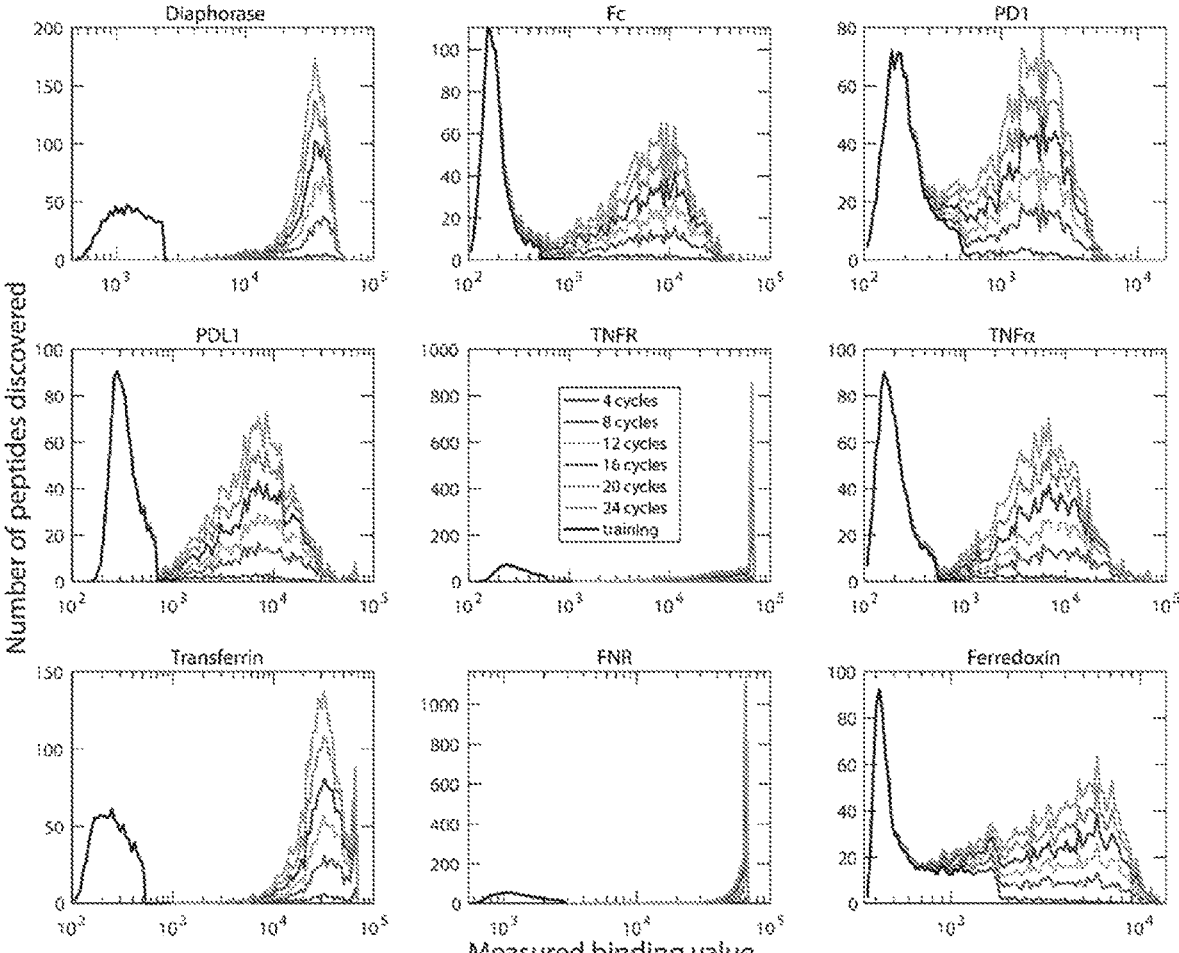
FIG. 37 is an example of iterative training of a neural network to discover strong binding peptides in accordance with some embodiments.
Figure 38:
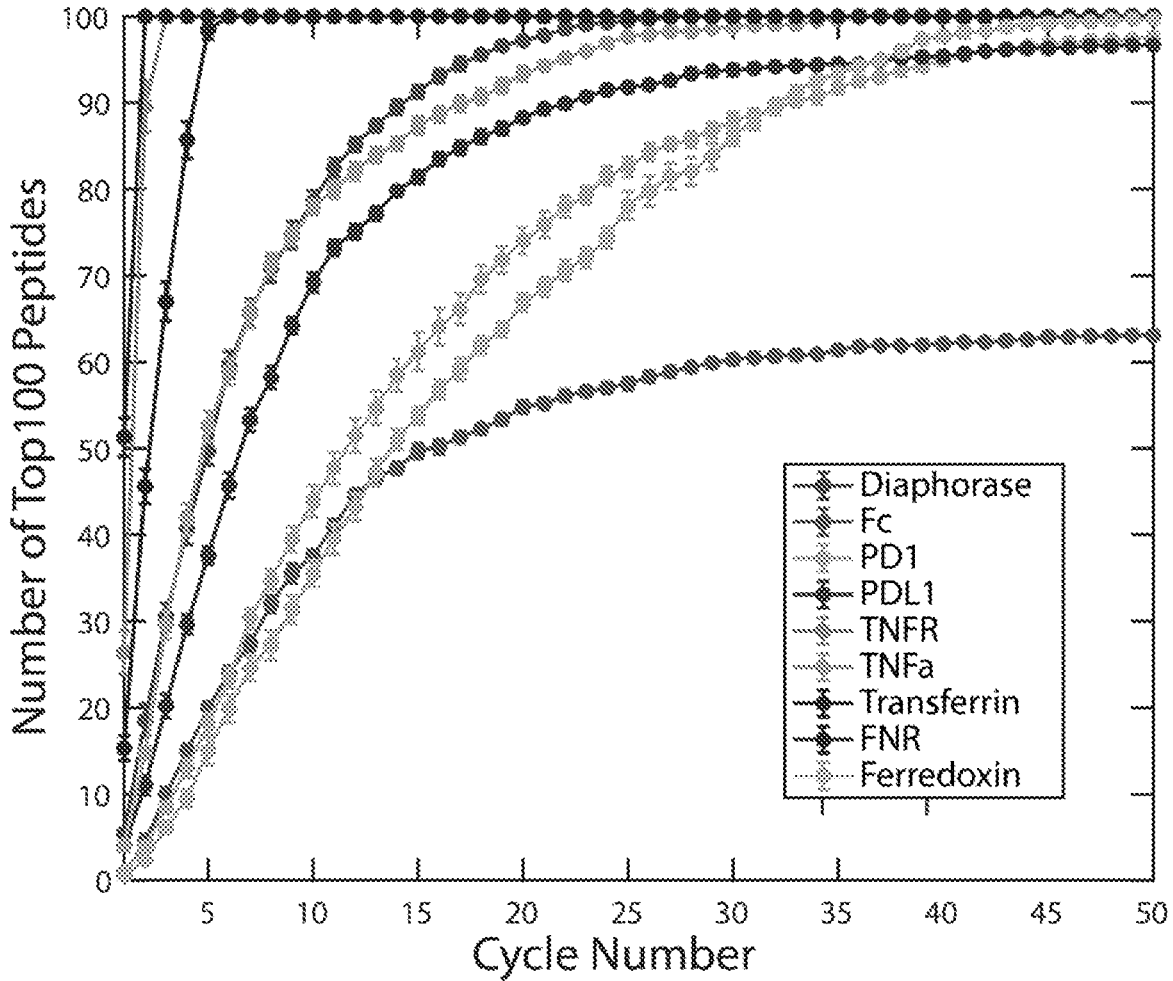
FIG. 38 is an example of the number of the top 100 peptides on an array discovered by a neural network as a function of learning cycle number for each of a set of proteins during an iterative optimization in accordance with some embodiments.

In FIG. 22, an example experiment for diaphorase binding is shown in accordance with some embodiments. As illustrated, the experiment started with 1000 weak binding sequences that were randomly selected from the array and used to predict 100 stronger binding sequences from the array. The measured values of these were then added to the training set and another 100 strong binding sequences were predicted, etc. As can be seen from the binding distribution vs. cycle number in FIG. 22, the growth in identified molecules was exclusively among the high binders, and after only ten rounds, almost 80 of the top 100 binding molecules in the library had been identified. Similar results were observed for all nine proteins tested, though with varying speeds of optimization (FIGS. 37-38). In some embodiments, this type of optimization can be performed for molecular libraries synthesized on commercial synthesizers which can make hundreds of molecules in a day. In addition to optimizing molecular recognition, additional filters such as solubility, toxicity in cell assays, off target binding, etc. can be added, providing a computationally accelerated route to molecular optimization.

FIGS. 12-14 show an example of a correlation of log 10 predicted peptide binding intensities with those measured on the peptide microarrays in accordance with some embodiments. More particularly, FIG. 12 shows that Diaphorase was incubated with arrays of ~126,000 unique and nearly random peptide sequences, and a relative binding value was recorded for each sequence. A neural network was trained on a random 90% of the sequence/binding value pairs and used to predict the target binding for the remaining 10% (validation set). The predictions for the test set are shown plotted against their measured values. FIG. 13 shows that this modeling procedure was performed 100 times for 9 different proteins, with the average correlation coefficients between the predicted and measured values tabulated (the error of the mean is shown) in accordance with some embodiments. FIG. 14 shows that the number of peptide sequences used to train the model was varied from 100 to 100,000, and the correlation coefficients between the measured and predicted values of the test set were recorded for each training set size in accordance with some embodiments. Training sets were randomly selected 10 times and error of the mean is shown.

In FIGS. 15A and 15B, a neural network was trained on a dataset of 90,000 peptide sequence/binding value pairs for both diaphorase and ferredoxin and the remaining ~36,000 sequence/binding value pairs were predicted (validation set) in accordance with some embodiments. FIG. 15A shows a scatter plot comparison of the measured ferredoxin and diaphorase binding values of the validation set. The color of each point is proportional to the difference between binding values for the two proteins for the sequence represented by that point (dark: ferredoxin>diaphorase, light: diaphorase>ferredoxin). FIG. 15B shows a comparison of the predicted binding values of the validation set for the two proteins. A point associated with a particular sequence in FIG. 15A has the same color in FIG. 15B, allowing one to track whether the points stay in the same positions within the scatter plot. The preservation of the shape and color positions between FIG. 15A and FIG. 15B means that the specificity of binding between the two proteins is captured in the neural network model.

FIG. 16 shows an example of the correlation between the predicted and measured values of the validation set vs. the number of amino acid descriptors used to represent each amino acid (average of 100 fits with randomized training sets, error of the mean is shown but generally smaller than the symbol) in accordance with some embodiments. 90% of the peptide sequences on an array incubated with diaphorase were used to train the model and 10% were used as the validation set.

FIG. 17 shows an example of a similarity matrix for binding to diaphorase from magnitude-normalized dot products calculated for each pair of amino acid vector representations in accordance with some embodiments. The number of vector descriptors was set to five in this case. The values represent an average of 100 fits with randomized training sets.

FIG. 18 shows an example of relative fit coefficients vs. number of amino acid descriptors for five different amino acid properties in accordance with some embodiments. The learned amino acid representations in FIG. 15A were used to fit the five different amino acid properties. The bottom line represents fits of sets of random numbers as a negative control (average of 100 random sets). For more details and data from other proteins see FIGS. 30-32.

FIG. 19 shows an example of the average autocorrelation of random walks (predicted binding values of 10,000 successive random single mutations) through sequence space starting at 500,000 randomly selected sequences for each protein in accordance with some embodiments.

In FIG. 20, an example model for diaphorase binding data was trained only on sequence/binding value pairs less than 2,000 counts (left dashed box) and used to predict binding of sequences with measured values up to 60,000 counts (right dashed box). The top 100 predicted sequences are shown in the top dashed box and average 40,000 counts in accordance with some embodiments.

FIG. 21 shows an example of a bar graph for amino acids vs correlation in accordance with some embodiments. The are arranged in three rows: front, closest to viewer; middle; and rear, furthest from viewer. The middle bars show that Diaphorase sequence/binding data was trained on sequences lacking a particular amino acid, using chemical properties of the amino acids as the descriptors in the encoder matrix; binding of the sequences containing that amino acid are predicted from its chemical properties and the correlation between predicted and measured is shown. The front row shows negative control in which random values were used as the fixed properties of the excluded amino acid instead of the literature values (100 sets of values averaged; error bars are about 0.01). The back row shows positive control in which the neural network was trained using 90% of the sequences that contain the amino acid in question and tested on the remaining 10%. Predicted vs. measured correlation is shown.

FIG. 22 shows a distribution of binding strengths as a function of optimization cycle number for diaphorase. 1000 weak binding sequences were used as the initial training set (left portion of graph) and for each cycle, the 100 strongest binding sequences were predicted and their measured values added to the training (red/purple (the portion of the graphs generally between 10,000 and 100,000 measure binding value counts). Inset: the percent of the 100 strongest binding sequences on the array that were discovered by the iterative process as a function of cycle number for 50 cycles.

FIG. 23 illustrates a sparse binary matrix representation of peptides (EQNSQVDG shown as an example) in accordance with some embodiments. The rows are the sequence positions, and in each row a 1 indicates which out of the 16 amino acids occupies that position. After the peptide sequence has terminated, the remaining rows (9-13 in the example above) are filled with zeros.

In some embodiments in accordance with FIG. 1B, the first layer of the neural network is an encoder that maps the sparse 13×16 peptide matrix (an example of which is shown in FIG. 23 in accordance with some embodiments) to a dense 13×N representation where N<16 (FIG. 24). This linear transformation can be performed by multiplying the sparse representation with a 16×N matrix whose weights are optimized during the training. The goal of the encoder is to preserve as much information about the sequences relevant to peptide binding as possible throughout the dimensionality reduction process. The neural network must therefore learn how to represent the amino acids in a continuous, real-valued space to avoid loss of information content as the amino acids are mapped to a lower dimension. Presumably, the real-value vector representations of each amino acid determined by the neural network contain some representation of the chemical features of the amino acids (e.g. charge, van der Waals radius, hydrophobicity . . . ), a concept explored below. Note, however, that the neural network is not confined by known chemical properties and any particular fit will generate a unique representation of the amino acids; the optimization is for a complete space, but the relative orientations of the vectors used as the basis for that space are not confined and thus vary from fit to fit. For greater dimensionality reduction (as one reduces the number of descriptors available to the network), the encoder is pressured further to learn an efficient set of real-valued vector representations of each amino acid optimized for peptide binding.

FIG. 24 illustrates an example of a dense matrix representation of peptides (EQNSQVDG shown as an example) in accordance with some embodiments. This matrix was generated by passing the sparse representation (FIG. 23) through the encoder portion of the neural network designed to reduce the dimensionality of the amino acid space to a real-valued space of N=5 descriptors. In general, the number of descriptors in the real-valued vector space encoded by the neural network can be any positive integer less than the number of amino acids (16 in this example).

After encoding each amino acid of the peptide sequence into a compact real-valued vector, all of the rows of the matrix are concatenated into a single vector. This vector is the real-valued space representation of the entire peptide sequence.

The peptide real-valued space vector is then passed through a feedforward neural network with two hidden layers with 100 nodes each and a bias term to predict the binding value. The rectified linear unit activation function is applied to the output of each hidden layer to introduce non-linearity into the model. A final output layer transforms the hidden layer representations into the predicted binding value, and no activation function is applied to this output.

Figures 25A, 25B, 25C:
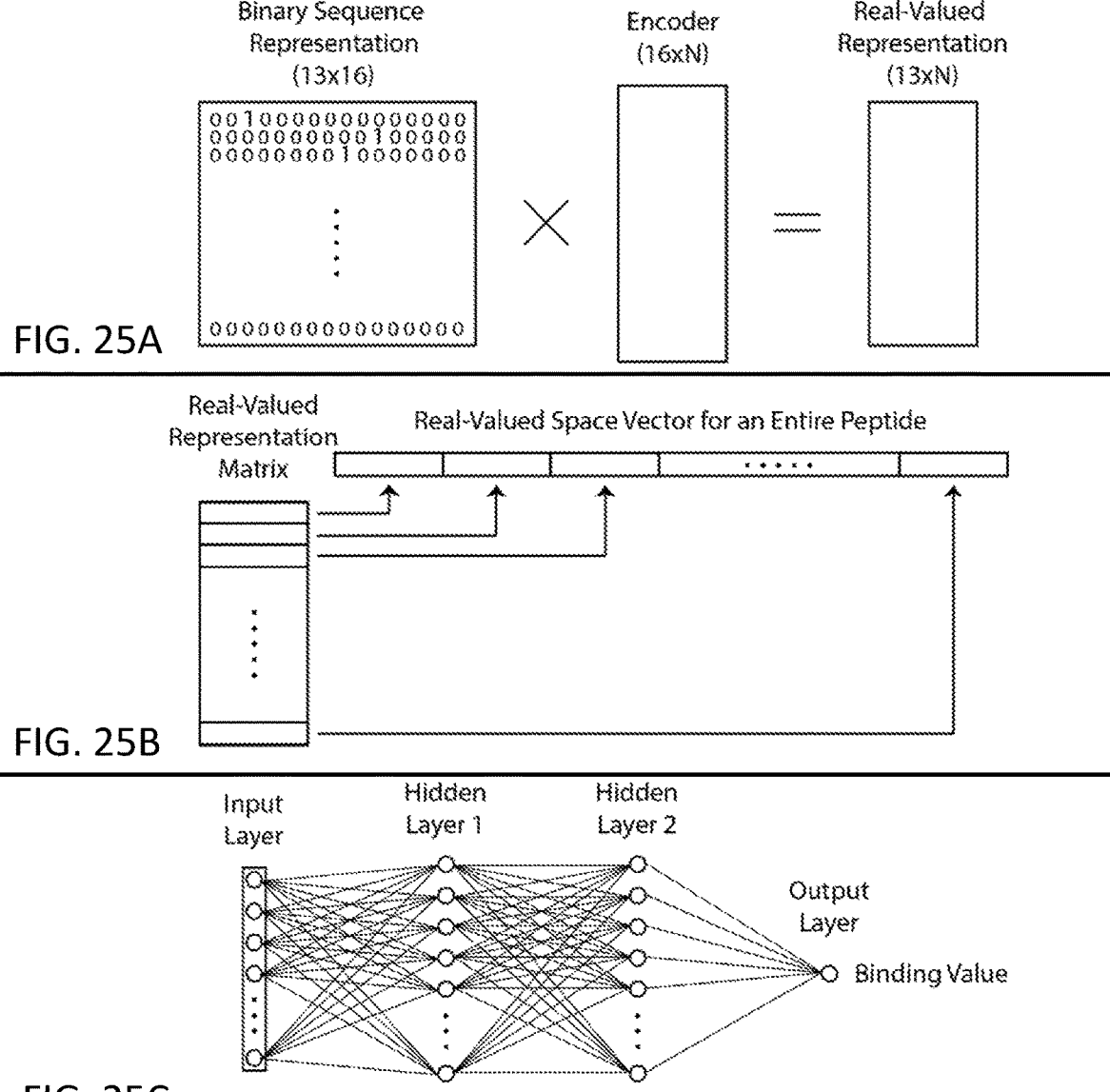
FIGS. 25A-25C are examples of a neural network architecture for predicting binding value from peptide sequence in accordance with some embodiments.

An example diagram of a neural network architecture is shown in FIGS. 25A, 25B, and 25C in accordance with some embodiments.

FIGS. 25A-C illustrate an example of a neural network architecture for predicting binding value from peptide sequence in accordance with some embodiments. FIG. 25A shows that a sparse binary representation of the peptide can undergo a linear transformation into the dense real-valued space representation by matrix multiplication with the encoder matrix that utilizes N descriptors in the vector representation of each amino acid in accordance with some embodiments. FIG. 25B shows that the matrix representation can be concatenated row-by-row, resulting in a real-valued space vector representation of the peptide in accordance with some embodiments. FIG. 25C shows that the real-valued space representation of the peptide can be passed through a feedforward neural network with two hidden layers to perform a non-linear prediction of the binding value from the sequence in accordance with some embodiments.

In an experiment in accordance with some embodiments, neural networks were created and optimized in PyTorch 0.4. From the ~125,000 sequences and measured binding values, 90% of the data was used to train the network and 10% was set aside to validate the trained model's performance unless stated otherwise. To avoid fitting the model to saturated data points (where the binding intensity exceeded the maximum measurable level of the detector) the top ~2% of the data was excluded from the training set (but included in the validation set). Some of the peptide arrays are synthesized in such a way that they have a GSG amino acid linker at the C-terminal end. This was removed from all sequences prior to analysis. Peptide binding was fit to $\log_{10}(counts+100)$, where "counts" is the raw fluorescence counts recorded by the fluorescence array scanner and 100 was added to suppress large fluctuations in the log due to noise and to avoid taking the log of zero. The distribution of binding strengths on a log scale is much closer to normal than on a linear scale, facilitating the fitting over the entire dynamic range of the data (100-300 fold).

The weights of the neural network were optimized by a mean squared error criterion with an Adam optimizer set to a learning rate of $10^{-3}$. Training was performed in 50,000 steps for all fits except those in FIGS. 22, 37, and 38 where 20,000 steps were used. A batch size of 100 sequences at a time was used in all fits. These sequences were not randomly selected, but rather sampled such that all binding values (in log scale) are equally represented in each batch, regardless of the actual distribution of values. This sampling method was found to improve the model's extrapolative performance in regions of very weak and very strong binding where little data exists, at the cost of its ability to interpolate in data-rich regions. No dropout was applied to any of the weights during training. Depending on the situation, the training and validation peptides were randomly chosen between 10 and 100 times and results averaged (The only exceptions are that the scatter plots in FIG. 27 are representative individual runs.)

The nine proteins used in this study are described in Table S1:

TABLE S1

| Protein* | Species | Source | Catalog # | MW (kDa) | Protein Format |
|---|---|---|---|---|---|
| Diaphorase | Human | Sigma | D1315 | 30.1 | Full Length |
| Ferredoxin | Spinach | Sigma | F3013 | 11.1 | Full Length |
| FNR | Spinach | Redding Lab** | | 35.3 | Full Length |
| PD1 | Human | Sinobiological | 10377-H02H | 42.7 | ECD-Fc*** |
| PDL1 | Human | Sinobiological | 10084-H02H | 52 | ECD-Fc*** |
| TNF alpha | Human | R&D Systems | 210-TA-100 | 17.5 | Full Length |
| TNFR2 | Human | R&D Systems | 1089-R2-025 | 20 | ECD**** |
| Transferrin | Human | Sigma | 90190 | 80 | Full Length |
| Fc | Human | Bethyl Labs | P80-104 | 26 | Digested IgG |

*FNR = Ferredoxin-NADP reductase, PD1 = Programmed Cell Death protein 1, PDL1 = Programmed Cell Death protein 1 Ligand, TNF alpha = Tumor Necrosis Factor alpha, TNFR = Receptor for TNF alpha, Fc = Fragment Cystallizable region of an IgG antibody
**Provided by Professor Kevin Redding, Arizona State University
***Fc-fused extracellular domain
****extracellular domain Table S2 shows which peptide array formats were used for each protein and summarizes the assay conditions:

TABLE S2

| Protein | Labeling | Array | Unique Peptides | Assay | Protein Conc. (nM) | # Technical Reps. (Corr)* |
|---|---|---|---|---|---|---|
| Diaphorase | HT-AF555 | HT-V13 | 126050 | HT-PROT | 10 | 3 (0.99) |
| Ferredoxin | HT-AF555 | HT-V13 | 126050 | HT-PROT | 10 | 3 (0.99) |
| FNR | HT-AF555 | HT-V13 | 126050 | HT-PROT | 10 | 3 (0.99) |
| PD1 | AF555 | CIMw189-s9 | 122926 | CIM-PROT | 1000 | 2 (0.94) |

TABLE S2-continued

| Protein | Labeling | Array | Unique Peptides | Assay | Protein Conc. (nM) | # Technical Reps. (Corr)* |
|---|---|---|---|---|---|---|
| PDL1 | AF555 | CIMw189-s9 | 122926 | CIM-PROT | 1000 | 2 (0.98) |
| TNF alpha | AF555 | CIMw189-s9 | 122926 | CIM-PROT | 1000 | 3 (0.95) |
| TNFR2 | AF555 | CIMw189-s9 | 122926 | CIM-PROT | 1000 | 3 (0.98) |
| Transferrin | AF555 | CIMw174-s3 | 122918 | CIM-PROT | 5000 | 2 (0.98) |
| Fc | AF555 | CIMw189-s9 | 122926 | CIM-PROT | 1000 | 2 (0.97) |

*The number of technical replicates averaged is shown as well as the correlation between them (average correlation if there were more than 2 replicates). Correlation is performed using the $\log_{10}(counts + 100)$ to be consistent with the rest of the analysis.

In the experiment, labeling of each of the proteins was similar. As an example, human diaphorase (NQO1) powder was reconstituted in water to 0.5 mg/mL and an 800 µL aliquot (~400 µg) was diluted with 50 µL 0.2 M $NaHCO_3$ just prior to labeling. A 100 µg aliquot of AlexaFluor 555 NHS ester (ThermoFisher cat. #A37571) was dissolved in 200 µL 0.2 M $NaHCO_3$, quickly transferred to the diaphorase solution and mixed well (final AF555-NHS concentration ~80 µM). The 1.0 mL solution was allowed to react at room temperature for 80 min then was loaded onto a PD MidiTrap G-25 columns (GE Healthcare) preequilibrated with 0.10 M $NH_4OAc$. The labeled protein was eluted in a single 1.5 mL fraction, aliquoted and frozen. MALDI MS analysis of the products showed a distribution of unlabeled, mono-, di-, and trilabeled products. Relative peak intensities indicated that >50% of the protein mixture was mono- or dilabeled (FIG. 26).

Figure 26:
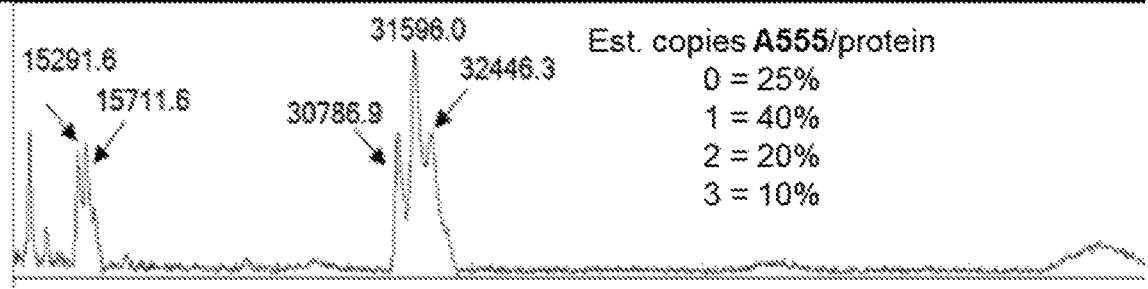
FIG. 26 is an example of MALDI MS spectra of AlexaFluor 555 labeled diaphorase shows a mixture of unlabeled, mono-, di-, and trilabeled products in accordance with some embodiments.

In FIG. 26, MALDI MS spectra of AlexaFluor 555 labeled diaphorase shows a mixture of unlabeled, mono-, di-, and trilabeled products.

Production quality arrays (HT-V13) were obtained from manufacturing following the removal of side-chain protection groups and vacuum sealed for storage under nitrogen until needed. On the day of assay, slides were loaded into a custom microarray cassette to enable use of 96 well SBS microtiter plate equipment. All liquid handling steps were accomplished with a Bravo liquid handling platform (Agilent, Santa Clara, CA). Arrays were hydrated with 81.0 µl per well PBST for 30 min at 57° C. Following return of the arrays to 37° C., 9.0 µl of diluted, labeled protein in PBST was added to each well and mixed. Labeled proteins were incubated on the array for 1 hour at 37° C. with mixing on a TeleShake95 (INHECO, Martinsried, Germany). Arrays were then washed three times in PBST followed by distilled water using a BioTek 405TS Select microtiter plate washer (BioTek Instruments, Inc., Winooski, VT). Slides were removed from the cassette, sprayed with isopropanol and centrifuged dry. Dried arrays were then imaged on an ImageXpress Micro XLS (Molecular Devices, San Jose, CA) at 532 nm excitation and 750 ms exposure. Feature level binding intensities were quantified using a library specific galfile in Mapix (Innopsys, Carbonne, France).

Protein binding assays were performed as follows. Briefly, high-density peptide microarrays were produced in the CIM Peptide Array core and contained 122,926 unique sequences of 5-mer to 12-mer peptides (average length: 10-mer), CIM-wafer 189. The peptide library in CIM-wafer 174 had 5 additional amino acids added to the C-terminus of shorter peptides and made all peptides 12-mers. Peptide microarrays were deprotected and the following day were blocked with 3% BSA in 1×PBST for 2 hours. Each protein was labeled with NHS-AlexaFluor555 (ThermoScientific) according to the manufacturer's protocol. The dye-to-protein ratio was adjusted so that each protein had from 0.5 to 3 dyes/protein molecule. Labeled protein samples were prepared as 1 μM solutions in 0.1% BSA in 1×PBST and incubated for 1 hour at room temperature with shaking. Arrays were washed 3 times with 1×PBST followed by 3 times with ddH$_2$O. Slides were dried by centrifugation and then imaged on an Innopsys Scanner and binding was quantified using Mapix.

FIG. 27 shows representative examples of predicted vs. measured binding values on a logarithmic scale for nine proteins for which experiments were performed. In each case 90% of the unique peptide sequence/binding value pairs on the array were used to train the network and the remainder were used as validation. Only the validation set is shown in the plots in FIG. 27; these are predictions of sequences that were never seen during the training and are effectively random samples from the entire 10$^{12}$ sized sequence space. Note that what is plotted is log$_{10}$(counts+100) to be consistent with the way the fits were performed.

FIG. 28 shows example correlation coefficients between the predicted and measured binding values plotted as a function of the training set size in accordance with some embodiments. As the number of peptides in the training set decreases, the neural network has a stronger tendency to overfit to the training data. Therefore, L1 weight regularization, where the mean of the absolute values of the weights is added as a term to the loss function, was applied during training. The weighting factor for the L1 regularization was optimized for each point in the graph to 0.1, 0.01, 0.001, 0.0001, or 0. Each point is the average of 10 independent training runs with randomly selected training and validation sets. The y-axis is the Pearson correlation coefficient calculated for the validation set comparing the predicted and measured values for those peptide sequences. Error bars are the error of the mean and are only larger than the symbol in the very smallest training sets.

Figure 29A:
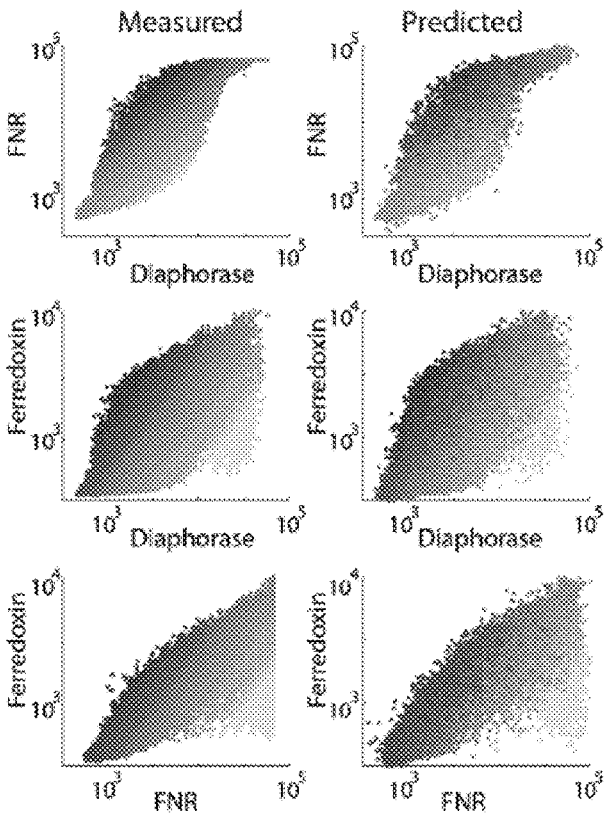
FIGS. 29A and 29B are examples of specific binding in accordance with some embodiments.
Figure 29B:
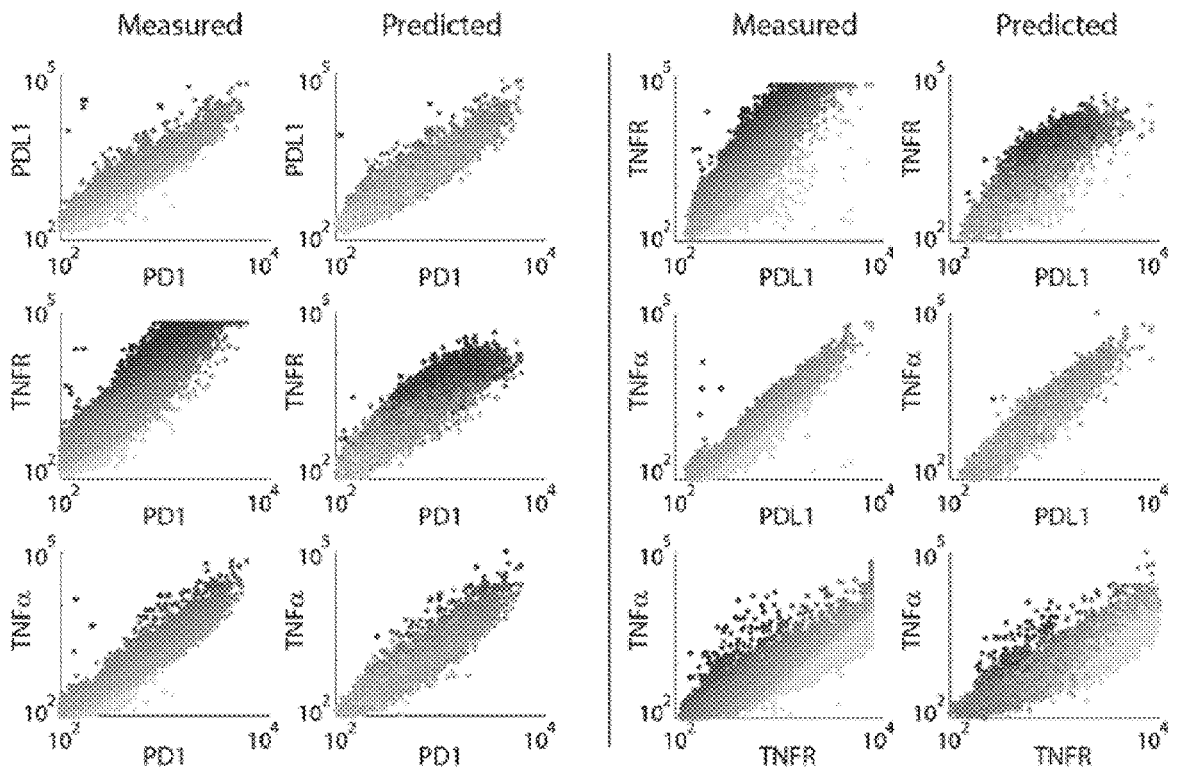

FIGS. 29A and 29B show examples of specific binding in accordance with some embodiments. More particularly, FIG. 29A shows the measured (left side) and predicted (right side) sequence binding values compared between all combinations of two proteins from the set diaphorase, FNR and ferredoxin. FIG. 29B shows similar comparisons between all combinations of PD1, PDL1, TNF alpha, and TNFR.

FIG. 30 shows an example of correlation coefficients between the predicted and measured binding values vs. the number of amino acid descriptors used in the encoder matrix in accordance with some embodiments. Each point is the average of 100 independent training runs and errors shown are errors of the mean (in most cases, the error is smaller than the symbol).

FIG. 31 shows examples of heat maps of the similarities between amino acid feature vectors learned by the neural network in accordance with some embodiments. Similarity is defined in this example as the cosine of the angle between the feature vectors (dot product normalized by the vector magnitudes). These similarity matrices were generated as an average of 100 training runs with 5 amino acid descriptors (the angle cosines were averaged).

Figure 32:
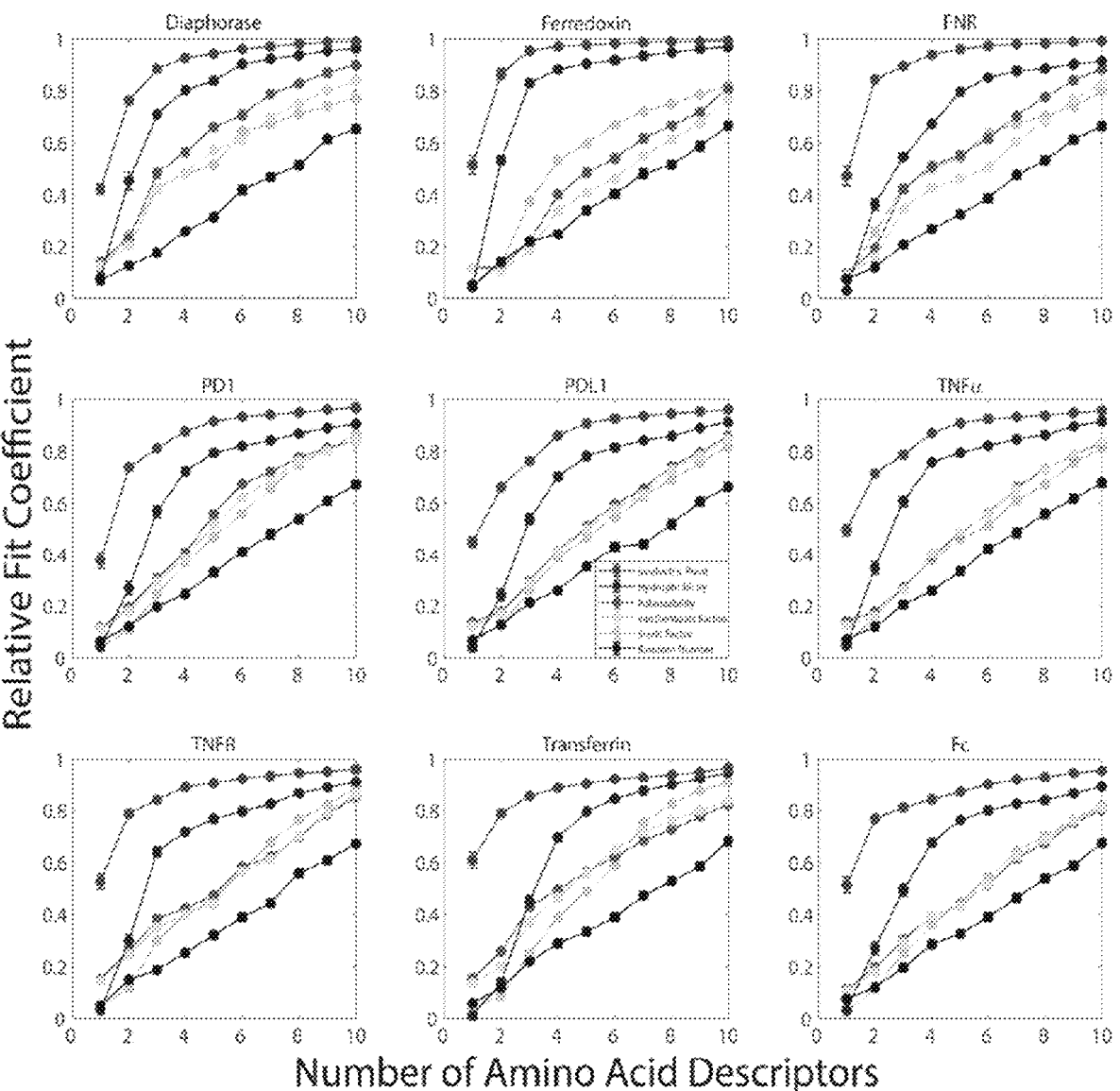
FIG. 32 is an example of $R^2$ fit values of the chemistry learned by the neural network fit to the measured chemical properties in accordance with some embodiments.

FIG. 32 shows an example of R$^2$ fit values of the chemistry learned by the neural network fit to the measured chemical properties in accordance with some embodiments. This analysis was run for a range of different numbers of amino acid descriptors. For each of 5 chemical properties, a linear fit was performed between the descriptor values and the property: P$_j$=c$_0$+Σ$_i$c$_i$d$_{i,j}$ where P$_j$ is the property in question for amino acid j, d$_{i,j}$ is the i$^{th}$ descriptor for the j$^{th}$ amino acid and c$_i$ is the associated fitting coefficient for the i$^{th}$ descriptor. The R$^2$ value for the fit is a measure of how much information about a given chemical property is encoded in the amino acid descriptors learned by the neural network. The projection of the encoder matrix onto a set of random numbers is used as a control for over-fitting. Each point is the result of 100 training runs individually fit and then averaged together. Error bars are the error of the mean and are frequently smaller than the symbols.

Figure 33:
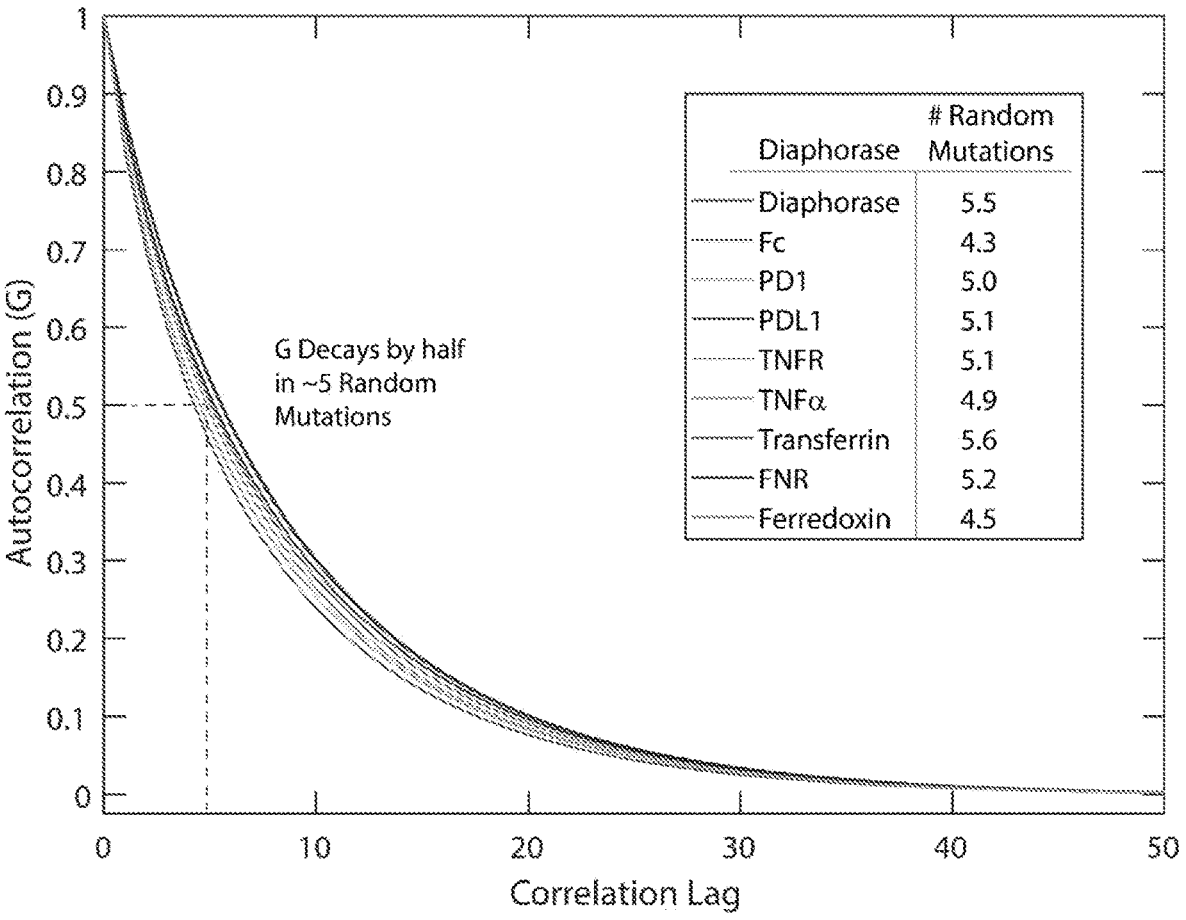
FIG. 33 is an example of an autocorrelation curve in accordance with some embodiments.

FIG. 33 shows an example, in accordance with some embodiments, of an autocorrelation curve:

$$G(k) = \frac{1}{c_0 M} \sum_{m=1}^{M-k} (y_m - \bar{y})(y_{m+k} - \bar{y})$$

of a trace that follows the log$_{10}$ predicted binding value during a random walk in which each step is a point mutation. Here, G is the autocorrelation as a function of the correlation lag in mutation steps during the random walk, k. M is the total number of steps, y$_m$ is the predicted binding for the sequence generated by the m$^{th}$ mutation in the series. c$_0$ is the sample variance. Starting with a randomly generated 10-amino acid peptide sequence, 10,000 randomly selected mutations are performed sequentially and for each mutation the binding is predicted from a fit of the binding data for a particular protein. The predicted binding values for this series of point mutations in the sequential random walk is essentially a one-dimensional representation of the topology of the molecular recognition landscape for a particular protein, and is used to generate an autocorrelation curve. The experiment was repeated 500,000 times for each protein (50,000 times for each of 10 independent neural network fits) and the average result is shown. The error of the mean is smaller than the width of the line. The number of mutations in the random walk required to decrease G to 0.5 is shown in the inset for each protein.

Figure 34:
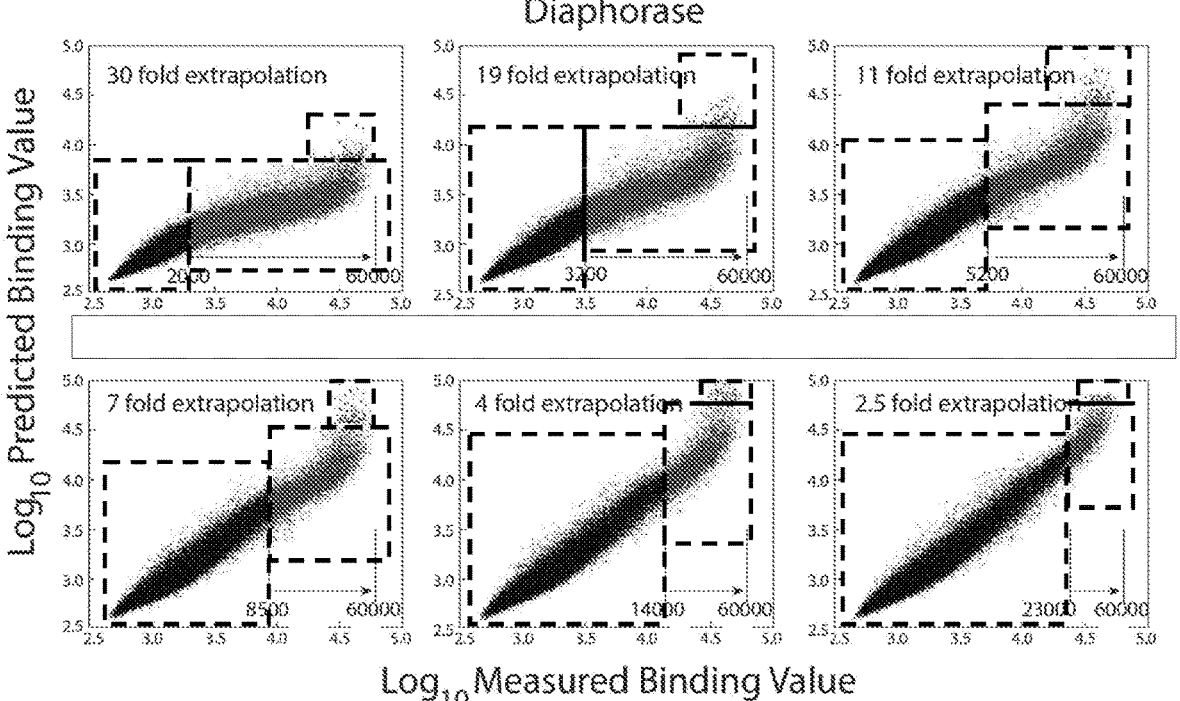
FIG. 34 is an example of extrapolations to peptide sequences that bind diaphorase more strongly than any of those observed in a training set in accordance with some embodiments.
Figure 35:
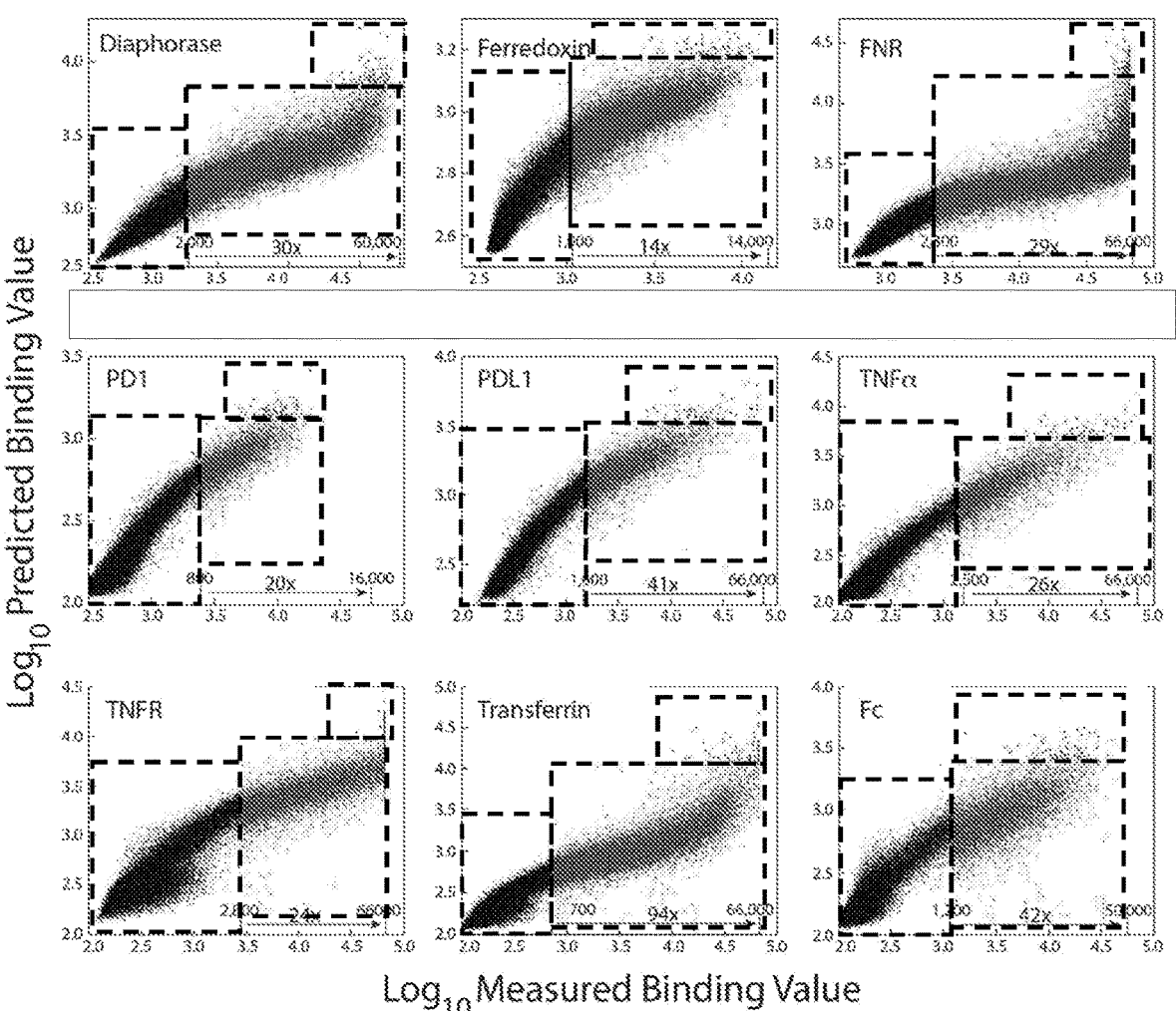
FIG. 35 is an example of extrapolations to peptide sequences that bind more strongly than any of those observed in a training set for models trained on all of a set of different protein targets in accordance with some embodiments.

FIG. 34 shows examples of extrapolations to peptide sequences that bind diaphorase more strongly than any of those observed in the training set in accordance with some embodiments. The extrapolative performance is shown for neural networks trained on different ranges of weak binding peptides. The training sets are in the left dashed boxes, the validation sets are in right dashed boxes, and the top 100 predicted binders are in the top boxes. The x and y axes are log$_{10}$ of the number of counts in each binding measurement and the values shown in each panel are the actual number of counts over which predictions are made. The larger the dynamic range of the training set, the more accurately the validation points are predicted, but even when training occurs on only the bottom 3% of the measured values, the top 100 predicted values average 20-fold higher than the highest value used in the training.

FIG. 35 shows examples of extrapolations to peptide sequences that bind more strongly than any of those observed in the training set for models trained on all of the different protein targets in accordance with some embodiments. The training set is in the left dashed box, the validation set is in the right dashed box, and the top 100 predicted binders are in the top dashed box. Note that the top predictions in every case are among the highest measured values and represent extrapolation over ranges between 14- and 94-fold. Note that in cases where the measurement saturates substantially (FNR, TNFR and transferrin), the highest values predicted are generally those in saturation. Note also that in a number of cases the points (sequences) that fit the worst form vertical lines. These are the cases where one of the averaged runs was saturated and the other one or two runs were much lower. This probably represents artifacts on the arrays that gave bright spots in one run for a few points (e.g., dust; we did not exclude any data in our analysis).

Figure 36:
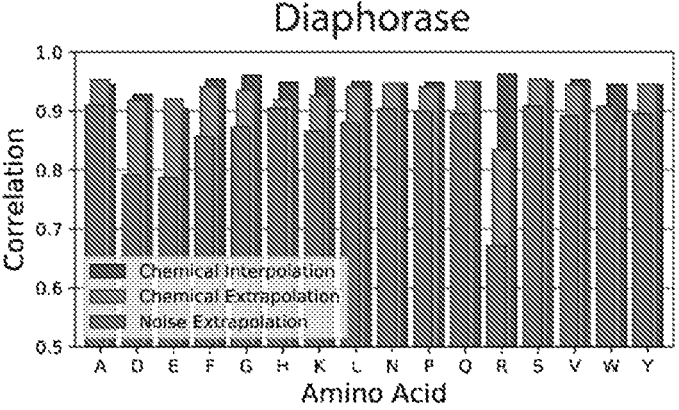
FIG. 36 is an example of chemical extrapolation to represent amino acids left out of a training set in accordance with some embodiments.
Figure 36:
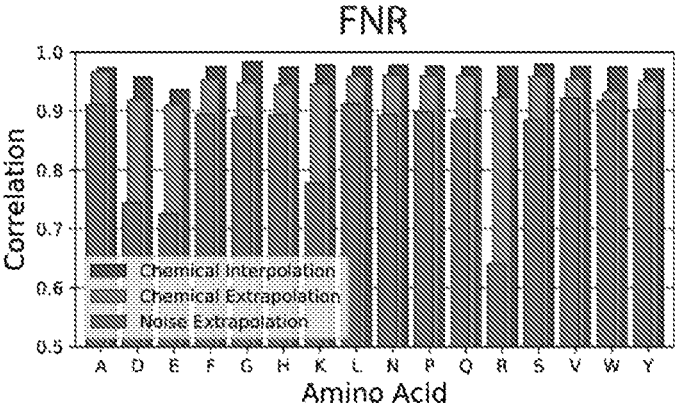
Figure 36:
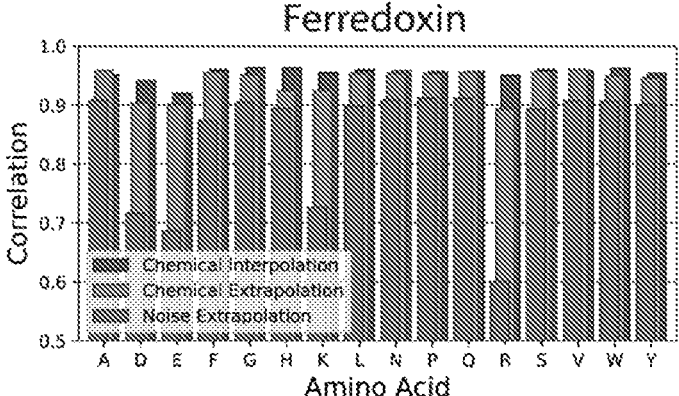

FIG. 36 shows examples of chemical extrapolation to represent amino acids left out of the training set in accordance with some embodiments. The encoder matrix was replaced with the isoelectric point, hydrophobicity, and van der Waals terms for the amino acids, and these values were fixed, forcing the neural network to learn the relationship between these physical-chemical properties and the corresponding binding value, effectively reducing a sequence of amino acids to a sequence of physical-chemical values. This should allow the neural network to learn chemistry and predict how other combinations of physical chemical values would behave in the array. To test this, a neural network was trained on all peptides without the amino acid indicated in the bar graph, replacing the sequence of amino acids with the sequence of three physical-chemical property values of amino acids present, and then validated on the remaining set of peptides that contain the amino acid in question. This forces the network to use the chemistry it learned from the other amino acids to predict what a new amino acid with a different set of physical-chemical values would do (middle row of bars). The correlation between predicted and measured values is plotted. As a negative control, the physical-chemical properties for the extrapolated amino acid were replaced with random numbers (front row of bars, repeated with 100 sets of random numbers). As a positive control, the neural network was trained and evaluated on the set of amino acids containing the amino acid (back set of bars, 90% train and 10% validation).

There are a number of observations that can be made with regard to FIG. 36. Here the network was forced to use three physical-chemical properties from the literature to represent each amino acid rather than choosing its own values. Looking first at the front row bars, where the chemical properties of a particular amino acid were replaced by random numbers, one learns which amino acids have the greatest effect on binding. Importantly, this usually means replacing the values for only one amino acid in the peptide with random numbers and thus one generally does not expect a huge effect, and in most cases, that is what is observed. The obvious exceptions are, not unexpectedly, the charged amino acids (D, E, K, R). The middle row bars represent what happens if one trains on the physical-chemical properties of the other amino acids, using peptide sequences that lack the amino acid in question, and then predict the binding to peptides containing that amino acids given its physical chemical properties. The network had to learn enough chemistry from the physical-chemical properties of the other 15 amino acids to predict what the binding would be to peptides containing an amino acid with a different combination of those physical-chemical properties. It does a pretty good job of learning about charge. From E, K and R, it learns enough about charge to predict what the charge values of D will mean in terms of binding. In fact, in almost all cases significant chemistry is learned (the error bars on the bar chart are not shown, they are <0.01). It has a hard time learning the chemistry of tryptophan, but this makes sense; where would it learn about indole rings? It never quite figures out what the effect of arginine should be, but where would it learn what a guanidinium group would do?

FIG. 37 shows examples of iterative training of a neural network to discover strong binding peptides in accordance with some embodiments. The model is initially trained on a weak binding subset of the data (dark curve on the left of each graph), and then asked to predict the top 100 binders on the peptide array. The measured binding values for these predicted peptides are added to the training set, and another 100 peptides is predicted, etc. The multicolored curves (on the right of each graph) represent the distribution of binding for the "discovered" sequences as a function of cycle number. This process is iterated for 50 cycles. Each experiment was repeated 10 times and averaged. In general, the curves are distinctly bimodal, with the high values increasing rapidly during the iterative optimization. For two of the proteins, TNFR and FNR, there were more than 100 sequences with saturating binding and thus essentially all of the predicted values are at or very near saturation.

FIG. 38 shows examples of the number of the top 100 peptides on the array discovered by the neural network as a function of learning cycle number for each of the proteins during the iterative optimization described in FIG. 37 in accordance with some embodiments. Each experiment was repeated 10 times and averaged and the error of the mean is shown when it is larger than the symbol. With the exception of Fc, all or almost all of the top 100 peptides are discovered within 50 cycles. In the case of Fc, looking at FIG. 35, one can see the issue. There are a series of points near saturation that are always predicted to be low. These points are likely artifacts (e.g., dust), as they have saturated binding in only one of the two replicates and low binding in the other (there are 34 such points in the dataset and a few others that are near saturating in one and low in the other). Thus, there is no way the network can predict them accurately because their average value is not consistent with the sequence dependence. Similarly, there are several such points in both PD1 (3 very high in one that are low in the other) and PDL1 (2 saturating in one and low in the other) which keep them from quite finding all 100 of the highest measured values. The rate at which TNFR, FNR and Transferrin increase with cycle is somewhat artificial. There are more than 100 measured binding values in saturation, so as long as one of the saturated values is found, it is counted as being in the top 100. As is apparent in FIG. 35, the prediction rapidly finds the values that are deep in saturation.

Example Embodiments

System, method, and media for molecule design using machine learning mechanisms are provided. In some embodiments, systems for proposing molecules having desired functional property values are provided. These systems include a memory and a hardware processor that is coupled to the memory. The hardware processor is configured to form a first training set for a neural network using, for each of a first plurality of known molecules, a plurality of input values that represent the structure of the known molecule and a plurality of functional property values for the known molecule. The hardware processor is then configured to train the neural network using the first training set. The hardware processor is next configured to propose a first plurality of proposed molecules, and predict first predicted functional property values of the first plurality of proposed molecules that have the desired function property values. The hardware processor is then configured to cause the first plurality of proposed molecules to be synthesized to form a first plurality of synthesized molecules. The hardware processor is next configured to receive first measured functional property values of the first plurality of synthesized molecules. The hardware processor is then configured to add data regarding the first plurality of synthesized molecules to the first training set to form a second training set and retrain the neural network using the second training set.

In some implementations of the system, the plurality of input values for each of the first plurality of known molecules are based on one-hot representations of building block molecules that form the known molecule.

In some implementations of the system, the building block molecules are amino acids.

In some implementations of the system, the known molecules are peptides.

In some implementations of the system, the plurality of input values for each of the first plurality of known molecules are based on chemical properties of building block molecules that form the known molecule.

In some implementations of the system, the neural network includes an encoder layer based on chemical properties of building block molecules that form the first plurality of known molecules.

In some implementations of the system, an iterative process is used to propose the first plurality of proposed molecules. In some implementations of the system, the iterative process attempts to find a local maximum based on each of the first plurality of proposed molecules.

In some implementations of the system, the hardware processor is further configured to: propose a second plurality of proposed molecules, and predict second predicted functional property values of the second plurality of proposed molecules that have the desired function property values; cause the second plurality of proposed molecules to be synthesized to form a second plurality of synthesized molecules; receive second measured functional property values of the second plurality of synthesized molecules; and determine whether the second measured functional property values a threshold amount different from the first measured functional property values.

In some embodiments, methods for proposing molecules having desired functional property values are provided. The methods form a first training set for a neural network using, for each of a first plurality of known molecules, a plurality of input values that represent the structure of the known molecule and a plurality of functional property values for the known molecule. Next, the methods train the neural network using the first training set using a hardware processor. The methods then propose a first plurality of proposed molecules, and predict first predicted functional property values of the first plurality of proposed molecules that have the desired function property values. Next, the methods cause the first plurality of proposed molecules to be synthesized to form a first plurality of synthesized molecules. Then, the methods receive first measured functional property values of the first plurality of synthesized molecules. Next, the methods add data regarding the first plurality of synthesized molecules to the first training set to form a second training set and retrain the neural network using the second training set.

In some implementations of the methods, the plurality of input values for each of the first plurality of known molecules are based on one-hot representations of building block molecules that form the known molecule.

In some implementations of the methods, the building block molecules are amino acids.

In some implementations of the methods, the known molecules are peptides.

In some implementations of the methods, the plurality of input values for each of the first plurality of known molecules are based on chemical properties of building block molecules that form the known molecule.

In some implementations of the methods, the neural network includes an encoder layer based on chemical properties of building block molecules that form the first plurality of known molecules.

In some implementations of the methods, an iterative process is used to propose the first plurality of proposed molecules. In some implementations of the methods, the iterative process attempts to find a local maximum based on each of the first plurality of proposed molecules.

In some implementations of the methods, the methods also: propose a second plurality of proposed molecules, and predict second predicted functional property values of the second plurality of proposed molecules that have the desired function property values; cause the second plurality of proposed molecules to be synthesized to form a second plurality of synthesized molecules; receive second measured functional property values of the second plurality of synthesized molecules; and determine whether the second measured functional property values a threshold amount different from the first measured functional property values.

In some embodiments, non-transitory computer-readable media containing computer executable instructions that, when executed by a processor, cause the processor to perform a method proposing molecules having desired functional property values are provided. In these non-transitory computer-readable media, the method includes forming a first training set for a neural network using, for each of a first plurality of known molecules, a plurality of input values that represent the structure of the known molecule and a plurality of functional property values for the known molecule. The method also includes training the neural network using the first training set. The method further includes proposing a first plurality of proposed molecules, and predicting first predicted functional property values of the first plurality of proposed molecules that have the desired function property values. The method also includes causing the first plurality of proposed molecules to be synthesized to form a first plurality of synthesized molecules. The method further includes receiving first measured functional property values of the first plurality of synthesized molecules. And the method includes adding data regarding the first plurality of synthesized molecules to the first training set to form a second training set and retrain the neural network using the second training set.

In some implementations of the non-transitory computer-readable media, the plurality of input values for each of the first plurality of known molecules are based on one-hot representations of building block molecules that form the known molecule.

In some implementations of the non-transitory computer-readable media, the building block molecules are amino acids.

In some implementations of the non-transitory computer-readable media, the known molecules are peptides.

In some implementations of the non-transitory computer-readable media, the plurality of input values for each of the first plurality of known molecules are based on chemical properties of building block molecules that form the known molecule.

In some implementations of the non-transitory computer-readable media, the neural network includes an encoder layer based on chemical properties of building block molecules that form the first plurality of known molecules.

In some implementations of the non-transitory computer-readable media, an iterative process is used to propose the first plurality of proposed molecules. In some implementations of the non-transitory computer-readable media, the iterative process attempts to find a local maximum based on each of the first plurality of proposed molecules.

In some implementations of the non-transitory computer-readable media, the method further includes: proposing a second plurality of proposed molecules, and predicting second predicted functional property values of the second plurality of proposed molecules that have the desired function property values; causing the second plurality of proposed molecules to be synthesized to form a second plurality of synthesized molecules; receiving second measured functional property values of the second plurality of synthesized molecules; and determining whether the second measured functional property values a threshold amount different from the first measured functional property values.

Accordingly, methods, systems, and media for molecule design using machine learning mechanisms are provided.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for proposing molecules having desired functional property values, comprising:
   a computerized synthesizer;
   a memory; and
   a hardware processor coupled to the computerized synthesizer and to the memory and configured to:
   form a first training set for a neural network by:
      selecting features of building block molecules to produce selected features and functional properties of a first plurality of proposed molecules that comprise the building block molecules to produce selected functional properties;
      accessing a library that identifies known molecules $A_{known}$ made from the building block molecules;
      forming a representation of the library in which each known molecule $A_{known}$ is shown as a matrix $B_{known}$ of representations of the building block molecules;
      forming a matrix T of the values V of the selected features of all of the building block molecules in the library or all of features of the building block molecules;
      multiplying each matrix $B_{known}$ by the matrix T to form a matrix $C_{known}$ of features;
      linearizing each matrix $C_{known}$ to form vectors $D_{known}$; and
      determining, for each vector $D_{known}$, known values $P_{known}$ for corresponding known molecules $A_{known}$ that comprise the selected functional properties;
   train the neural network using at least the vectors $D_{known}$ of the first training set to predict values $P_{known}$ of the selected function properties to produce a trained neural network;
   propose a first plurality of proposed molecules $A_{proposed}$; and predict values $P_{proposed}$ of the selected functional properties of the proposed molecules $A_{proposed}$ using the trained neural network;
   synthesize selected molecules of the first plurality of proposed molecules $A_{proposed}$ to form a first plurality of synthesized molecules $A_{synth}$ using the computerized synthesizer;
   receive first measured functional property values of the first plurality of synthesized molecules $A_{synth}$; and
   add data regarding selected molecules of the first plurality of synthesized molecules $A_{synth}$ to the library used to form the first training set to form a second training set and retrain the neural network using the second training set.

2. The system of claim 1, wherein the representation of the library is based on one-hot representations of the building block molecules that form the known molecules $A_{known}$, wherein the one-hot representations are formed using one-hot encoding of the building block molecules.

3. The system of claim 2, wherein the building block molecules are amino acids.

4. The system of claim 1, wherein the known molecules $A_{known}$ are peptides.

5. The system of claim 1, wherein the representation of the library is based on chemical properties of building block molecules that form the known molecules $A_{known}$.

6. The system of claim 1, wherein the neural network includes an encoder layer based on chemical properties of building block molecules that form the known molecules $A_{known}$.

7. The system of claim 1, wherein an iterative process is used to propose the first plurality of proposed molecules.

8. The system of claim 7, wherein the iterative process attempts to find a local maximum based on each of the first plurality of proposed molecules.

9. The system of claim 1, wherein the hardware processor is further configured to:
   propose a second plurality of proposed molecules, and predict second predicted functional property values of the second plurality of proposed molecules that have desired function property values;
   synthesize selected molecules of the second plurality of proposed molecules to form a second plurality of synthesized molecules using the computerized synthesizer;
   receive second measured functional property values of the second plurality of synthesized molecules; and
   determine whether the second measured functional property values a threshold amount different from a first measured functional property values.

10. A method for proposing molecules having desired functional property values, comprising:
   forming a first training set for a neural network by:
      selecting features of building block molecules to produce selected features and functional properties of a first plurality of proposed molecules that comprise the building block molecules to produce selected functional properties;
      accessing a library that identifies known molecules $A_{known}$ made from the building block molecules;
      forming a representation of the library in which each known molecule $A_{known}$ is shown as a matrix $B_{known}$ of representations of the building block molecules;
      forming a matrix T of the values V of the selected features of all of the building block molecules in the library or all of features of the building block molecules;

multiplying each matrix $B_{known}$ by the matrix T to form a matrix $C_{known}$ of features;

linearizing each matrix $C_{known}$ to form vectors $D_{known}$; and determining, for each vector $D_{known}$, known values $P_{known}$ for corresponding known molecules $A_{known}$ that comprise the selected functional properties;

training the neural network using at least the vectors $D_{known}$ of the first training set using a hardware processor to predict values $P_{known}$ of the selected function properties to produce a trained neural network;

proposing a first plurality of proposed molecules $A_{proposed}$, and predict values $P_{proposed}$ of the selected functional properties of the proposed molecules $A_{proposed}$ using the trained neural network;

synthesizing selected molecules of the first plurality of proposed molecules $A_{proposed}$ to form a first plurality of synthesized molecules $A_{synth}$ using a computerized synthesizer;

receiving first measured functional property values of the first plurality of synthesized molecules $A_{synth}$; and adding data regarding selected molecules of the first plurality of synthesized molecules $A_{synth}$ to the library used to form the first training set to form a second training set and retrain the neural network using the second training set.

11. The method of claim 10, wherein the representation of the library is based on one-hot representations of the building block molecules that form the known molecules $A_{known}$, wherein the one-hot representations are formed using one-hot encoding of the building block molecules.

12. The method of claim 11, wherein the building block molecules are amino acids.

13. The method of claim 10, wherein the known molecules $A_{known}$ are peptides.

14. The method of claim 10, wherein the representation of the library is based on chemical properties of building block molecules that form the known molecules $A_{known}$.

15. The method of claim 10, wherein the neural network includes an encoder layer based on chemical properties of building block molecules that form the known molecules $A_{known}$.

16. The method of claim 10, wherein an iterative process is used to propose the first plurality of proposed molecules.

17. The method of claim 16, wherein the iterative process attempts to find a local maximum based on each of the first plurality of proposed molecules.

18. The method of claim 10, further comprising:

propose a second plurality of proposed molecules, and predict second predicted functional property values of the second plurality of proposed molecules that have desired function property values;

synthesize selected molecules of the second plurality of proposed molecules to form a second plurality of synthesized molecules using the computerized synthesizer;

receive second measured functional property values of the second plurality of synthesized molecules; and determine whether the second measured functional property values a threshold amount different from a first measured functional property values.

19. A non-transitory computer-readable medium containing computer executable instructions that, when executed by a processor, cause the processor to perform a method proposing molecules having desired functional property values, the method comprising:

forming a first training set for a neural network by:

selecting features of building block molecules to produce selected features and functional properties of a first plurality of proposed molecules that comprise the building block molecules to produce selected functional properties;

accessing a library that identifies known molecules $A_{known}$ made from the building block molecules;

forming a representation of the library in which each known molecule $A_{known}$ is shown as a matrix $B_{known}$ of representations of the building block molecules;

forming a matrix T of the values V of the selected features of all of the building block molecules in the library or all of features of the building block molecules;

multiplying each matrix $B_{known}$ by the matrix T to form a matrix $C_{known}$ of features;

linearizing each matrix $C_{known}$ to form vectors $D_{known}$; and determining, for each vector $D_{known}$, known values $P_{known}$ for corresponding known molecules $A_{known}$ that comprise the selected functional properties;

training the neural network using at least the vectors $D_{known}$ of the first training set using a hardware processor to predict values $P_{known}$ of the selected function properties to produce a trained neural network;

proposing a first plurality of proposed molecules $A_{proposed}$, and predict values $P_{proposed}$ of the selected functional properties of the proposed molecules $A_{proposed}$ using the trained neural network;

synthesizing selected molecules of the first plurality of proposed molecules $A_{proposed}$ to form a first plurality of synthesized molecules $A_{synth}$ using a computerized synthesizer;

receiving first measured functional property values of the first plurality of synthesized molecules $A_{synth}$; and adding data regarding selected molecules of the first plurality of synthesized molecules $A_{synth}$ to the library used to form the first training set to form a second training set and retrain the neural network using the second training set.

20. The non-transitory computer-readable medium of claim 19, wherein the representation of the library is based on one-hot representations of the building block molecules that form the known molecules $A_{known}$, wherein the one-hot representations are formed using one-hot encoding of the building block molecules.

21. The non-transitory computer-readable medium of claim 20, wherein the building block molecules are amino acids.

22. The non-transitory computer-readable medium of claim 19, wherein the known molecules $A_{known}$ are peptides.

23. The non-transitory computer-readable medium of claim 19, wherein the representation of the library is based on chemical properties of building block molecules that form the known molecules $A_{known}$.

24. The non-transitory computer-readable medium of claim 19, wherein the neural network includes an encoder layer based on chemical properties of building block molecules that form the known molecules $A_{known}$.

25. The non-transitory computer-readable medium of claim 19, wherein an iterative process is used to propose the first plurality of proposed molecules.

26. The non-transitory computer-readable medium of claim 25, wherein the iterative process attempts to find a local maximum based on each of the first plurality of proposed molecules.

27. The non-transitory computer-readable medium of claim 19, wherein the method further comprises:

propose a second plurality of proposed molecules, and predict second predicted functional property values of the second plurality of proposed molecules that have desired function property values;

synthesize selected molecules of the second plurality of proposed molecules to form a second plurality of synthesized molecules using the computerized synthesizer;

receive second measured functional property values of the second plurality of synthesized molecules; and determine whether the second measured functional property values a threshold amount different from a first measured functional property values.

* * * * *